(12) United States Patent
Nadeau et al.

(10) Patent No.: US 8,916,349 B2
(45) Date of Patent: Dec. 23, 2014

(54) ASSAY METHOD FOR TARGET NUCLEIC ACID BY SIGNAL AMPLIFICATION USING PROBE HYBRIDIZATION AND RESTRICTION

(75) Inventors: Jim Nadeau, Ellicott City, MD (US); Tobin Hellyer, Westminster, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 234 days.

(21) Appl. No.: 13/511,269

(22) PCT Filed: Nov. 23, 2010

(86) PCT No.: PCT/US2010/057781
§ 371 (c)(1),
(2), (4) Date: Aug. 16, 2012

(87) PCT Pub. No.: WO2011/063388
PCT Pub. Date: May 26, 2011

(65) Prior Publication Data
US 2012/0322067 A1 Dec. 20, 2012

Related U.S. Application Data

(60) Provisional application No. 61/263,596, filed on Nov. 23, 2009.

(51) Int. Cl.
*C12Q 1/68* (2006.01)
(52) U.S. Cl.
CPC .............. *C12Q 1/682* (2013.01); *C12Q 1/6813* (2013.01); *C12Q 1/6823* (2013.01)
USPC ....................................................... 435/6.11
(58) Field of Classification Search
None
See application file for complete search history.

(56) References Cited

U.S. PATENT DOCUMENTS

| | | | |
|---|---|---|---|
| 4,766,062 | A | 8/1988 | Diamond et al. |
| 5,451,503 | A | 9/1995 | Hogan et al. |
| 5,846,726 | A | 12/1998 | Nadeau et al. |
| 5,866,336 | A | 2/1999 | Nazarenko et al. |
| 5,876,930 | A | 3/1999 | Livak et al. |
| 5,919,630 | A | 7/1999 | Nadeau et al. |
| 5,925,517 | A | 7/1999 | Tyagi et al. |
| 5,935,791 | A | 8/1999 | Nadeau et al. |
| 6,391,593 | B1 | 5/2002 | Weston et al. |
| 6,743,582 | B2 | 6/2004 | Nadeau et al. |
| 6,887,662 | B1 | 5/2005 | Alajem et al. |
| 2004/0142369 | A1 | 7/2004 | Alajem et al. |
| 2006/0088856 | A1 | 4/2006 | Sorge et al. |
| 2010/0279295 | A1 | 11/2010 | Roy et al. |

FOREIGN PATENT DOCUMENTS

| | | | |
|---|---|---|---|
| CN | 101215600 | A | 7/2008 |
| CN | 101250593 | A | 8/2008 |
| CN | 101328498 | A | 12/2008 |
| EP | 0878554 | A2 | 11/1998 |
| JP | 2007075023 | A | 3/2007 |
| WO | 2007041774 | A1 | 4/2007 |
| WO | 2007060707 | A2 | 5/2007 |
| WO | 2008013462 | A2 | 1/2008 |
| WO | 2009055366 | A1 | 4/2009 |
| WO | 2010030716 | A1 | 3/2010 |

OTHER PUBLICATIONS

Flores-Munguia et al., "Performance assessment of eight high-throughput PCR assays for viral load quantitation of oncogenic HPV types", Journal of Molecular Diagnostics, vol. 6 No. 2, May 2004, p. 115-124.
Griffin et al., "Recognition of thymine-adenine base pairs by guanine in a pyrimidine triple helix motif", Science, vol. 245, Aug. 1989, pp. 967-971.
Hesselink et al., "Comparison of three different PCR methods for quantifying human papillomavirus type 16 DNA in cervical scrape specimens", Journal of Clinical Microbiology, Sep. 2005, vol. 43, No. 9, p. 4868-4871.
Hoogsteen, "The structure of crystals containing a hydrogen-bonded complex of 1-methylthymine 9-methyladenine", Acta Cryst. (1959) vol. 12, 822-823.
Lane et al., "The thermodynamic advantage of DNA oligonucleotide stacking hybridization reactions: energetics of a DNA nick", Nucleic Acids Research, 1997, vol. 25, No. 3, 611-616.
Lillo et al., "Determination of human papillomavirus (HPV) load and type in high-grade cervical lesions surgically resected from HIV-infected women during follow-up of HPV infection", Clinical Infectious Deseases, 2005; vol. 40, No. 3, p. 451-457.
Markham et al., DINAMelt web server for nucleic acid melting prediction, Nucleic Acids Research, 2005, vol. 33, Web Server Issue W577-W581.
Markham et al., "UNAFold: Software for nucleic acid folding and hybridization", Bioinformatics, vol. II: Structure, Function and Applications, vol. 453, ©2008, http://www.bioinfo.rpi.edu/applications/hydrid/download.php, pp. 3-31.
Moberg et al., "Real-time PCR-based system for simultaneous quantification of human papillomavirus types associated with high risk of cervical cancer", Journal of Clinical Microbiology, Jul. 2003, vol. 41, No. 7, p. 3221-3228.
Payan et al., "Human papillomavirus quantification in urine and cervical samples by using the Mx4000 and LightCycler general Real-Time PCR SystemsÑ", Journal of Clinical Microbiology, Mar. 2007, vol. 45, No. 3, p. 897-901.
Peitsaro et al., "Integrated human papillomavirus type 16 is frequently found in cervical cancer precursors as demonstrated by a novel quantitative real-time PCR technique", Journal of Clinical Microbiology, Mar. 2002, vol. 40, No. 3, p. 886-891.
Sanger et al., DNA sequencing with chain-terminating inhibitors, Proc. Natl. Acad. Sci. USA, vol. 74, No. 12, pp. 5463-5467, Dec. 1977.

(Continued)

*Primary Examiner* — James Martinell
(74) *Attorney, Agent, or Firm* — Lerner, David, Littenberg, Krumholz & Mentlik, LLP

(57) ABSTRACT

Oligonucleotides for detection of nucleic acid in a sample that provide for an amplified signal by recycling probes and probe fragments.

34 Claims, 16 Drawing Sheets

(56) References Cited

OTHER PUBLICATIONS

Spargo et al., "Detection of M. tuberculosis DNA using Thermophilic Strand Displacement Amplification", Molecular and Cellular Probes (1996) 10, 247-256.

Tucker et al., "Real-time PCR-based fluorescent assay for quantitation of human papillomavirus types 6, 11, 16, and 18", Molecular Diagnosis vol. 6 No. 1, 2001, p. 39-47.

Yakovchuk et al., "Base-stacking and base-pairing contributions into thermal stability of the DNA double helix", Nucleic Acids Research, 2006, vol. 34, No. 2, 564-574.

Zhu et al., "Development of a base stacking hybridization-based microarray method for rapid identification of clinical isolates", Diagnostic Microbiology and Infectious Desease 59 (2007) 149-156.

Amicarelli G. et al: "Genotype-Specific Signal Generation Based on Igestion of 3-Way DNA Junctions: Application to KRAS Variation Detection", Clinical Chemistry, American Association for Clinical Chemistry, Washington, DC, vol. 52, No. 10, Jan. 1, 2006, pp. 1855-1863, XP008075059.

Extended European Search Report for Application No. EP10832359 dated Jun. 13, 2013.

Nadeau J. G. et al: "Real-Time, Sequence-Specific Detection of Nucleic Acids During Strand Displacement Amplification", Analytical Biochemistry, Academic Press Inc, New York, vol. 276, No. 2, Dec. 15, 1999, pp. 177-187, XP000906307.

International Search Report PCT/US2010/057781, dated Aug. 31, 2011.

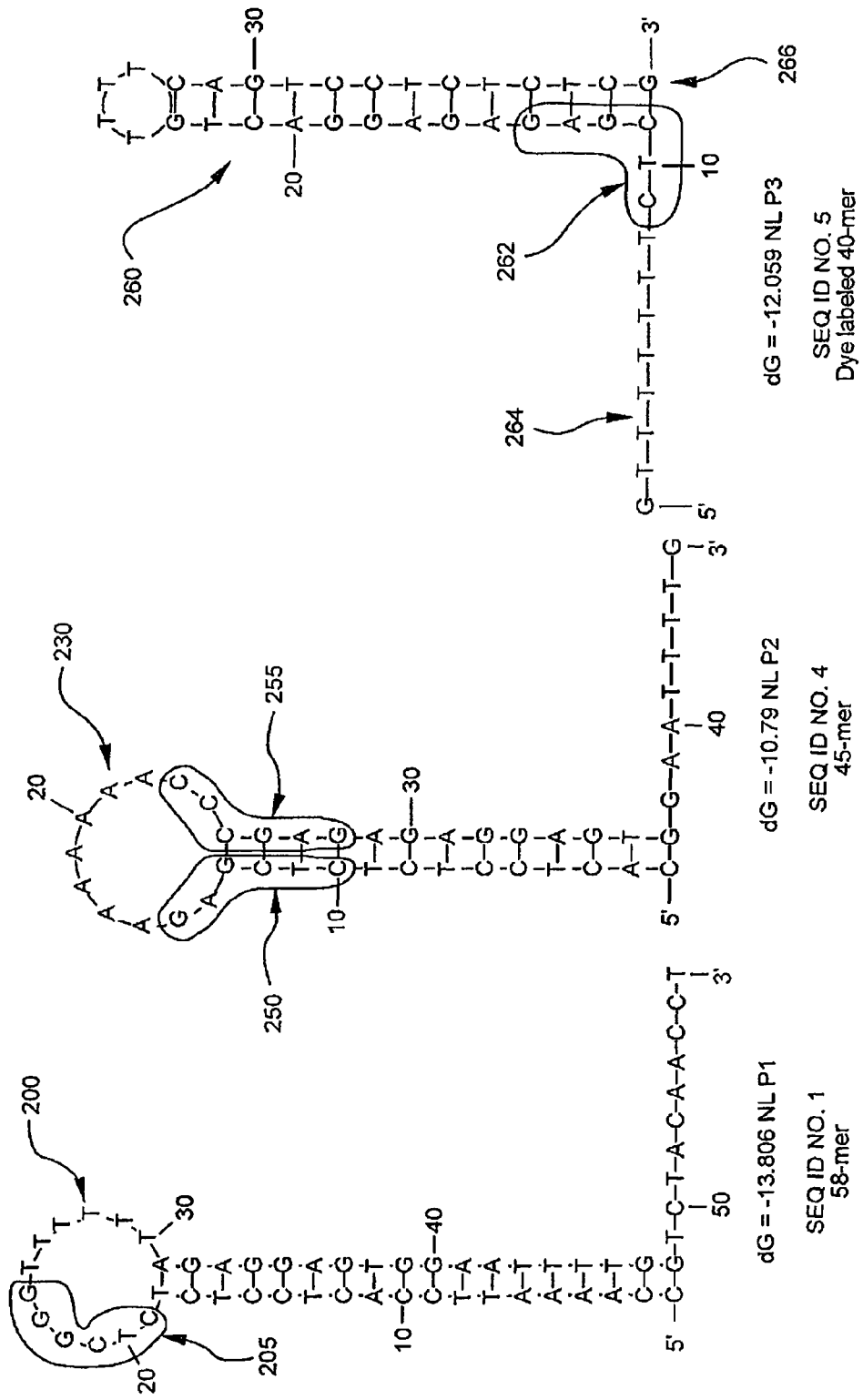

FIG. 7A

HPV type 16  5'...GTGTGCCTCCTGGGGAGGTTGTAGACCAAAATTCCAGTCCTCCAAAATA...3' SEQ ID NO:2

FIG. 7B

HPV type 58  5'...AACTGGCAGACGGAGGAGGTGtTAaACCAAAtTgCCAGTCCTCCAAAATA...3' SEQ ID NO:3

ASSAY METHOD FOR TARGET NUCLEIC ACID BY SIGNAL AMPLIFICATION USING PROBE HYBRIDIZATION AND RESTRICTION

CROSS-REFERENCE TO RELATED APPLICATIONS

This application is a national phase entry under 35U.S.C. §371 of International Application No. PCT/US2010/057781 filed Nov. 23, 2010 published in English as International Publication No. WO 2011/063388, which claims the benefit of the filing date of U.S. Provisional Patent Application No. 61/263,596 filed Nov. 23, 2009, the disclosures of which are hereby incorporated herein by reference.

FIELD AND BACKGROUND OF THE INVENTION

The present invention relates to oligonucleotide probes and methods for the detection of target nucleic acid sequences in a sample. More particularly, the present invention relates to oligonucleotide probes which, only when hybridized to target nucleic acid sequences, can be cleaved. Cleaving the probes either directly or indirectly leads to both signal generation and signal amplification by recycling of the probes.

The identification of a target nucleic acid sequence is of great importance in both biological research and medical diagnostics. Detection of a target sequence can be used to identify and/or type a specific DNA or RNA molecule and to uncover mutations.

Numerous methods and techniques exist in the art with which detection and/or identification of a target sequence can be effected. For example, polynucleotide sequencing methods can be used to determine the nucleotide sequence of a target DNA or RNA molecule. The methods typically used for sequencing include the Sanger dideoxy method, see, e.g., Sanger et al. *Proc. Natl. Acad. Sci.* USA, 74:5463-5467 (1977), or the Maxam and Gilbert method. See, e.g., Maxam et al, Methods in Enzymology, 65:499-559 (1980).

The polymerase chain reaction (PCR) can also be used to detect the presence of a target sequence in a sample. PCR utilizes oligonucleotide primers which specifically bind regions within the target sequence to amplify the target nucleic acid sequence, the generation of amplification products is indicative of the presence of the target sequence.

Another approach to target nucleic acid identification involves hybridizing an oligonucleotide probe to the target nucleic acid sequence wherein hybridization is indicative of the presence thereof.

An oligonucleotide probe binds to a target nucleic acid by forming hydrogen bonds between bases in the target and the oligonucleotide. Common B-DNA has conventional adenine-thymine (A-T) and guanine-cytosine (G-C) Watson and Crick base pairs with two and three hydrogen bonds formed therebetween, respectively. Conventional hybridization technology is based upon the capability of sequence-specific DNA or RNA oligonucleotide probes to bind to a complementary target nucleic acid via Watson-Crick hydrogen bonds. However, other types of internucleotide hydrogen bonding patterns are known wherein atoms not involved in Watson-Crick base pairing to a first nucleotide can form hydrogen bonds to another nucleotide. For example, thymine (T) can bind to an AT Watson-Crick base pair via hydrogen bonds to the adenine, thereby forming a T-AT base triad. Hoogsteen, *Acta Crystallographica* 12:822 (1959) first described the alternate hydrogen bonds present in T-AT and C-GC base triads. More recently, G-TA base triads, wherein guanine hydrogen bonding with a central thymine has been observed. Griffin et al., *Science,* 295:967-971 (1989).

Oligonucleotide probes which can bind to a target nucleic acid with both Watson-Crick and non-Watson-Crick hydrogen bonds form extremely stable complexes with the target nucleic acid and as such have a variety of research and diagnostic utilities.

For example, oligonucleotides can be used as probes for target nucleic acids that are immobilized onto a filter or membrane, or are present in tissues, e.g. as described in Sambrook et al., *Molecular Cloning: A Laboratory Manual*, Vols. 1-3, (1989). However, the oligonucleotide probes described in this reference are limited by their poor binding stability and selectivity.

Another example includes solution phase detection methods. Several solution-phase detection methods, sometimes referred to as homogeneous assays, are known. The term "homogeneous" is used in the art to refer to methods performed without separating unhybridized oligonucleotide probes from probe-target hybrids. These methods often rely upon the fact that the fluorescence of many fluorescent labels can be affected by the conformation of the oligonucleotide probe or by the immediate chemical environment.

U.S. Pat. No. 5,876,930 to Livak et al. discloses a method for identifying a target nucleic acid sequence. The method utilizes an oligonucleotide probe which includes a fluorescent reporter molecule and a quencher molecule capable of quenching the fluorescence of the reporter molecule. The oligonucleotide probe according to this method is constructed such that the probe exists in at least one single-stranded conformation when unhybridized, where the quencher molecule is near enough to the reporter molecule to quench the fluorescence of the reporter molecule. The oligonucleotide probe also exists in at least one conformation when hybridized to a target nucleic acid where the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, this method enables the presence of a specific target nucleic acid sequence to be determined based on a change in the fluorescence intensity of the reporter molecule, the quencher molecule, or a combination thereof. The limitation of this approach is that no signal amplification is enabled, resulting in inability of detecting low target concentrations. In addition, this method is inherently characterized by a high background signal.

U.S. Pat. No. 5,925,517 to Tyagi et al. discloses unimolecular and bimolecular hybridization probes for the detection of nucleic acid target sequences. The probes include a target complement sequence, an affinity pair holding the probe in a closed conformation in the absence of target sequence, and either a label pair that interacts when the probe is in the closed conformation or, for certain unimolecular probes, a non-interactive label. Hybridization of the target and target complement sequences shifts the probe to an open conformation. The shift is detectable due to reduced interaction of the label pair or by decreasing a signal from a non-interactive label. Certain unimolecular probes can discriminate between target and non-target sequences differing by as little as one nucleotide. The limitation of this approach is that no signal amplification is enabled, resulting in inability of detecting low target concentrations. In addition, this method is inherently characterized by a high background signal.

U.S. Pat. No. 5,866,336 to Nazarenko et al. describes labeled nucleic acid amplification oligonucleotides, which can be linear or hairpin primers or blocking oligonucleotides. The oligonucleotides disclosed by Nazarenko are labeled with donor and/or acceptor moieties of molecular energy transfer pairs. The moieties can be fluorophores, such that fluorescent energy emitted by the donor is absorbed by the acceptor. The acceptor may be a fluorophore that fluoresces at a wavelength different from the donor moiety, or it may be a non-fluorescent dark quencher. These oligonucleotides are configured so that a donor moiety and an acceptor moiety are incorporated into the amplification product. The invention also provides methods and kits for directly detecting amplification products employing the nucleic acid amplification primers. When labeled linear primers are used, treatment with exonuclease or by using specific temperature eliminates the need for separation of unincorporated primers. This "closed-tube" format greatly reduces the possibility of carryover contamination with amplification products, provides for high throughput of samples, and may be totally automated.

U.S. Pat. No. 4,766,062 to Diamond et al. describes a diagnostic reagent containing a complex of a probe polynucleotide bound via purine/pyrimidine hydrogen bonding to a labeled polynucleotide. The probe contains a target binding region capable of binding to a target sequence of a biological sample. Diamond et al. further describes a method in which contact with a sample containing the target nucleotide sequence causes binding, initially between the target and a single-stranded portion of the target binding region of the probe. Thereafter the labeled polynucleotide is displaced from the resulting complex. Detection of the displaced labeled polynucleotide gives a value that is a function of the presence and concentration of target nucleotide sequence in the sample.

U.S. Pat. No. 5,451,503 to Hogan et al. describes nucleic acid hybridization probes having at least one nucleic acid strand which has at least two separate target specific regions that hybridize to a target nucleic acid sequence, and at least two distinct arm regions that do not hybridize with the target nucleic acid but possess complementary regions that are capable of hybridizing with one another. These regions are designed such that, under appropriate hybridization conditions, the complementary arm regions will not hybridize to one another in the absence of the target nucleic acid; but, in the presence of target nucleic acid the target-specific regions of the probe will anneal to the target nucleic acid, and the complementary arm regions will anneal to one another, thereby forming a branched nucleic acid structure which is useful for target nucleic acid sequence detection. U.S. Pat. No. 6,887,662 to Alajem et al. presents itself as an improvement over what is described in Hogan et al. in that the target nucleic is released and made available for subsequent amplification cycles.

Although the above mentioned methods are less complicated to perform than simple oligonucleotide probe detection methods such as that described by Sambrook et al. in which oligonucleotide probes are used to target nucleic acids that are immobilized onto a filter or membrane, some limitations still apply. For example, a method which is simple to perform such as that described by Livak et al. can yield false positive results since hybridization to non-target sequences will also yield, in some cases, a positive result.

In general, the above methods are characterized by low signal and high background. Hogan et al. teaches signal amplification by template recycling and background reduction by appropriate selection of the length of the arm regions of the oligonucleotides employed thereby. Methods which are aimed at producing more accurate results are oftentimes more complicated to perform.

Detection of oncogenic human papillomavirus (HPV) presents a significant challenge due to the multitude of associated genotypes and heterogeneity of the HPV genome. Currently there are only two FDA-approved screening assay for high risk strains of HPV (the Hybrid Capture 2 High-Risk HPV DNA Test (digene HC2) from Qiagen; Cervista HPV from Hologic). The HC2 assay utilizes multiple long RNA-based probes to overcome sequence variations in the target DNA and ensure comprehensive strain coverage. By the nature of this design, however, the Digene assay suffers from poor specificity and exhibits cross-reaction with various low risk genotypes of HPV. Other assays for detection of HPV that are based on amplification of nucleic acid targets are complicated by the need to employ degenerate primers and probes to account for sequence heterogeneity. When mixed together, such cocktails of oligonucleotides are prone to non-specific primer interactions that can lead to the generation of short amplicons of primer dimers and which detract from the efficiency of target-specific amplification and detection. This is among the reasons why real-time probe-based amplification and detection of HPV DNA is not widely practiced and is generally restricted to detection of either individual genotypes such as described in Flores-Munguia, Roberto, et al, "Performance Assessment of Eight High-Throughput PCR Assays for Viral Load Quantitation of Ocongenic HPV Types," *Journal of Molecular Diagnostics*, Vol. 6, No. 2, pp. 115-124 (May 2004); Hesselink, A. T., et al, "Comparison of Three Different PCR Methods for Quantifying Human Papillomavirus Type 16 DNA in Cervical Scrape Specimens," *Journal of Clinical Microbiology*, Vol. 43, No. 9, p. 4868-4871 (September 2005); Tucker, Ruth Ann et al, "Real-time PCR-based Fluorescent Assay for Quantiation of Human Papillomavirus Types 6, 11, 16, and 18, *Molecular Diagnosis*, Vol. 6, No. 1, pp. 39-47 (2001) or a limited multiplex assay format involving detection of up to three genotypes in single reaction such as described in Moberg, Martin, et al., "Real-Time PCR-Based System for Simultaneous Quantification of Human Papillomavirus Types Associated with High Risk of Cervical Cancer" *Journal of Clinical Microbiology*, Vol. 41, No. 7, pp. 3221-3228 (July 2003); Peitsaro, Panu et al, "Integrated Human Papillomavirus Type 16 Is Frequently Found in Cervical Cancer Precursors as Demonstrated by a Novel Quantitative Real-Time PCR Technique," *Journal of Clinical Microbiology*, Vol. 40, No. 3, pp. 886-891 (2002). Real-time detection of PCR amplification products using the intercalating dye SYBR green has been reported but this technology lacks adequate specificity for reliable clinical diagnosis and typically requires melt curve analysis for accurate interpretation of positive results. This assay is described in Lillo, F. B., et al, "Determination of Human Papillomavirus (HPV) Load and Type in High-Grade Cervical Lesions Surgically Resected from HIV-Infected Women during Follow-up of HPV Infection," *Clinical Infectious Diseases*, Vol. 40, pp. 451-457 (2005) and Payan, C., et al., "Human Papillomavirus Quantification in Urine and Cervical Samples by Using the Mx4000 and Light Cycler General Real-Time PCR Systems, *Journal of Clinical Microbiology*, Vol. 45, No. 3 p. 897-901 (2007).

In addition to the assay design limitations imposed by potential interactions between primers and probes, currently available PCR instruments offer no more than four to six optical channels for detection of multiplexed reactions. As a result, specific detection of all fourteen high risk genotypes of HPV typically requires multiple separate PCRs, which limits instrument throughput and has potentially negative impact on upstream specimen processing, assay quality control and reagent manufacture.

Consequently, an assay and method for detecting high risk strains of HPV in a single multiplexed reaction using a common optical channel is sought. Improved methods for signal amplification and background reduction are also sought for detecting moderately high to high abundance nucleic acid target sequences (e.g., DNA from high risk strains of HPV) in a format that is amenable to high degrees of multiplexing and that do not require use of a promiscuous DNA polymerase enzyme which can lead to false positive results.

SUMMARY OF THE INVENTION

This invention relates to oligonucleotide probes and method for detecting target nucleic acids using a homogenous, isothermal, multiplex-compatible signal amplification system. In one embodiment, the target nucleic acid is present in a concentration that is moderately high to high. The method described herein is referred to as Signal Amplification by Probe Hybridization and Restriction (SAPHyR).

In preferred embodiments, the method utilizes the well characterized single stranded DNA nicking activity of a restriction endonuclease. One example of restriction endonuclease is the enzyme BsoBI. Relationships between reaction temperatures and probe melting temperatures are selected to cause cyclical generation of cleaved oligonucleotide fragments. These fragments further trigger secondary cyclical cleavage reactions to generate signal (fluorescent).

In one embodiment, the method detects the presence or absence of a target nucleic acid in a sample by preparing a sample suspected of containing a target nucleic acid. Methods for preparing samples for assays that will detect target nucleic acid, if present, are well known to those skilled in the art and not discussed in detail herein. One example of nucleic acid extraction from sample is the BD Viper™ System with XTR™ technology from Becton Dickinson (BD) located in Franklin, Lakes N.J.

The extracted nucleic acid from the sample is combined with a reaction mixture having first and second oligonucleotide probes, and a sequence specific endonuclease, wherein the first and second oligonucleotide probes each have a first sequence and a second sequence. The first sequences of the first and second oligonucleotide probes are complementary with non-overlapping sequences of the target nucleic acid. The second sequences of each of the first and second oligonucleotide probes are complementary with each other and form a duplex restriction site recognized by the sequence specific endonuclease. At least one of the first and second oligonucleotide probes has a detectable label positioned at one side of the restriction site and a quenching moiety positioned at the other side of the restriction site. This relative positioning allows the first sequences of the first and second oligonucleotide probes to selectively hybridize with the non-overlapping sequences of the target nucleic acid and the second sequences of the first and second oligonucleotide probes to selectively hybridize with each other. The hybridization of these probes forms the duplex restriction site, such that, if the target nucleic acid is present in the sample, the sequence specific endonuclease cleaves the duplex at the restriction site. Cleaving the probes in this manner allows for detection of the label. Cleaving the probes also denatures the remaining portion of the oligonucleotide probes from the target nucleic acid and from each other.

In a second embodiment the prepared sample is combined into a reaction mixture that also has first, second, and third oligonucleotide probes, and a sequence specific endonuclease. The first and second oligonucleotide probes each have a first sequence and a second sequence. The first sequences of the first and second oligonucleotide probes are complementary with non-overlapping sequences of the target nucleic acid. The second sequences of each of the first and second oligonucleotide probes are at least partially complementary with each other, and form a duplex restriction site when the probes hybridize to the target, thereby bringing the first and second probes into proximity with each other. Preferably, at least one of the first and second probes have a hairpin configuration when not hybridized to the target sequence, thereby ensuring that the probes do not hybridize with each other in the absence of the target nucleic acid. The first and second oligonucleotide probes are non-labeled, and the second oligonucleotide probe also has a third sequence. At least a portion of the third sequence forms a hairpin with the second sequence of the second oligonucleotide probe that prevents the second oligonucleotide probe from hybridizing with the first oligonucleotide probe when the first and second oligonucleotide probes are not bound to the target nucleic acid. At least a portion of the third sequence hybridizes with the third oligonucleotide probe to form a duplex restriction site. The third oligonucleotide probe is a non-target specific oligonucleotide probe that has a detectable label positioned at one side of a first sequence that hybridizes with the third sequence of the second oligonucleotide probe to form the duplex restriction site. The third oligonucleotide probe also has a quenching moiety positioned at the other side of the first sequence of the third oligonucleotide probe.

In this embodiment, if the target nucleic acid is present in the sample, the first sequences of the first and second oligonucleotide probes are allowed (by denaturing of the hairpin structures) to selectively hybridize with the non-overlapping sequences of the target nucleic acid. Denaturation of the hairpin loop permits hybridization between the second sequences of the first and second oligonucleotide probes, cleavage of the previously formed duplex at the restriction site by the sequence specific endonuclease, and separation of the third sequence from the second oligonucleotide probe, and dissociation of the first and second oligonucleotide probes from the target nucleic acid. The following then occur in the reaction mixture in a plurality of cycles: i) hybridization of the third sequence of the second oligonucleotide probe with the third oligonucleotide probe, thus forming a chemically modified duplex restriction site, ii) nicking a single strand of the chemically modified duplex restriction site by the sequence specific restriction endonuclease, iii) liberating label from quencher, and iv) dissociation of the third oligonucleotide probe from the third sequence of the second oligonucleotide probe. The label so liberated is then detected using conventional technology for detecting the presence of a detectable label (e.g. a fluorophore), whereby the detection of signal indicates the presence of the target nucleic acid in the sample.

A third embodiment, described with reference to FIGS. 4 A-D, combines the extracted nucleic acid suspected of containing target nucleic acid with a first oligonucleotide probe (P1) having a first sequence and a second sequence, a second oligonucleotide probe (P2) having a first sequence and a second sequence, and a third oligonucleotide probe (P3) having a first sequence and a second sequence; and a sequence specific endonuclease.

For clarity, the sequences in this embodiment are described in terms of the schematic sequence designations in FIGS. 4 A-D). These designations are not intended to imply sequence composition or sequence length, but are merely provided as a link between the sequence descriptions and their schematic representation. In this embodiment, the first oligonucleotide probe (P1) has a first sequence (b'-i') that is complementary with a target nucleic acid sequence and a second sequence (a-c') that is complementary with the first sequence (a'-f') of the second oligonucleotide probe (P2). The first portion (d-e) of the second sequence (a-c') of the first probe is a single stranded chemically modified portion of a restriction site. Chemically modified restriction sites are described in greater detail herein. A portion of the first (b'-i') sequence and all of the second (a-c') sequence of the first oligonucleotide probe (P1) form a secondary structure (e.g., a hairpin).

The second oligonucleotide probe (P2) is a probe that does not hybridize directly to the target (although it may have a few target-specific nucleotides, the length of the target-specific sequence is too short to form stable hybrids with the target under reaction conditions), wherein a portion (d'-e') of the first sequence (a'-f') of the second probe (P2) is complementary to the single stranded chemically modified portion (d-e) of the second sequence (a-c') of the first probe (P1). The second sequence (b-e') of the second oligonucleotide probe is complementary with the first sequence (b'-e) of the third oligonucleotide probe (P3) wherein a portion (d-e) of the second sequence (b-e') of the second probe is a single stranded chemically modified portion of a restriction site. The first sequence and the second sequence of the second oligonucleotide probe partially overlap (e'-f') and wherein at least portions of the first sequence (portion b'-d') and second sequence (portion b-e') of the second oligonucleotide probe form a secondary structure (e.g., a hairpin).

The third oligonucleotide probe (P-3) is a probe that does not hybridize directly to the target (although it may have a few target-specific nucleotides, the length of the target-specific sequence is too short to form stable hybrids with the target under reaction conditions), wherein the first sequence (b'-e) includes a portion (d'-e') that is complementary to the single stranded chemically modified portion (d-e) of a restriction site of the second oligonucleotide probe (P2) and further comprising a detectable label (264) or quencher (266) moiety positioned thereon and the second sequence (d-k) forms a hairpin loop with a portion (b'-d') of the first sequence (b'-e) and has a detectable label (264) or quencher moiety (266) positioned thereon such that the quencher moiety blocks signal from the detectable label due to their relative positions in the third oligonucleotide probe.

In this embodiment, if the target nucleic acid is present in the sample, the target nucleic acid and the first sequence (b'-i') of the first oligonucleotide probe (P1) are allowed to selectively hybridize to form a first complex (P1: T). Furthermore, the method, in a plurality of cycles allows i) at least a portion (a-f) of the second sequence (a-c') of the first oligonucleotide probe (P1) and the first sequence (a'-f') of the second oligonucleotide probe (P2) to selectively hybridize to form a second complex (P2:P1:T); ii) cleaving a single strand portion (d'-e') of the duplex restriction site formed by the hybridization of the portion (d-e) of the second sequence (a-c') of the first oligonucleotide probe that forms the chemically modified single strand of the duplex restriction site with the complementary sequence (a'-f') on the second probe (P2) thereby separating the second sequence (b-e') of the second oligonucleotide probe from the non-overlapping portion (a'-d') of the first sequence of the second oligonucleotide probe (P2); and iii) dissociation of the second oligonucleotide probe from the first complex (P1:T).

Furthermore, according to this embodiment and, in a plurality of cycles, i) allowing the second sequence (b-e') of the second oligonucleotide probe (P2) to selectively hybridize with the first sequence (b'-e) of the third oligonucleotide probe (P3) to form a third complex thereby separating label from quencher and liberating signal, ii) cleaving a single strand (d'-e') duplex restriction site formed by hybridization of the portion (b-e') of the second sequence of the second oligonucleotide probe with the complementary sequence (b'-e) on the first sequence of the third oligonucleotide probe, iii) liberating label from quencher and dissociating the second sequence (b-e') of the second oligonucleotide probe from the remainder of the third oligonucleotide probe (P3). In this method signal generated from the label is detected, which indicates the presence of the target nucleic acid in the sample.

BRIEF DESCRIPTION OF THE DRAWINGS

FIG. 5 illustrates one example of the three probes described in FIGS. 4A-4D;

FIG. 7A illustrates the target sequence for HPV-16;

FIG. 7B illustrates the target sequence for HPV-58.

DETAILED DESCRIPTION

Figure 1A:
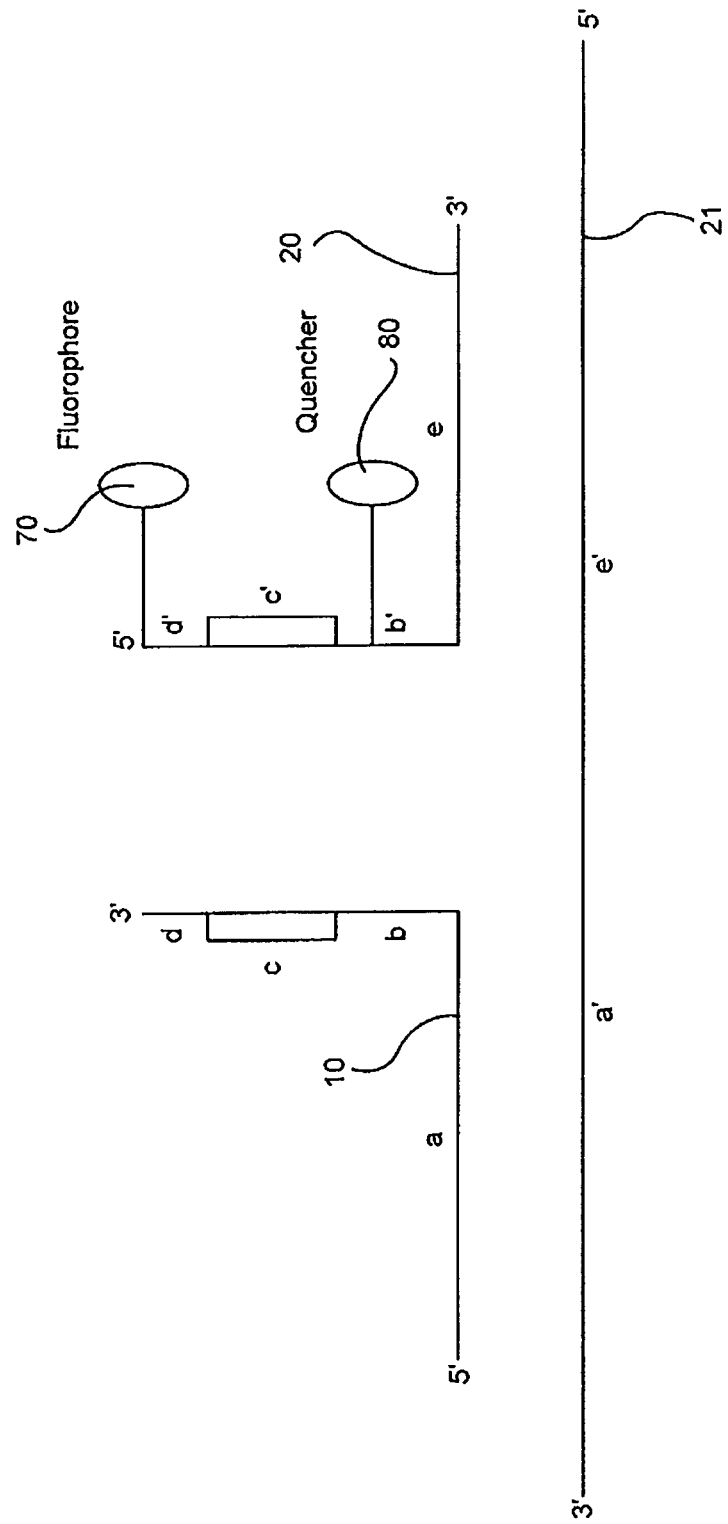
FIGS. 1A and 1B illustrate one embodiment of the present invention that utilizes two target specific probes and the complex that the two probes form with the target nucleic acid.

The present invention is directed to a set of oligonucleotides and a method employing the set of oligonucleotides that can be used for the detection of target nucleic acid sequences. Specifically, the method of the present invention can be used to detect the presence or absence of a specific target nucleic acid sequence by utilizing oligonucleotide probes which, when annealed to the template sequence(s), form an intrinsic (endogenous) cleavage site therebetween. Subsequent cleavage of this cleavage site leads to the generation of a detectable signal and also dissociates one or more of the oligonucleotide(s) from the target nucleic acid sequence, and as such allows template recycling and signal amplification.

The principles and operation of the oligonucleotides and methods according to the present invention may be better understood with reference to the drawings and accompanying descriptions.

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phraseology and terminology employed herein is for the purpose of description and should not be regarded as limiting.

As used herein the terms "oligonucleotide" and "probe" and the phrase "oligonucleotide probe" are used interchangeably to refer to a single stranded nucleic acid molecule or assembly of single stranded nucleic acid molecules which can exhibit one or more partial double stranded conformations. Such molecule(s) can be used according to the present invention for the detection of the presence or absence of a single stranded or a double stranded (following appropriate denaturation) target nucleic acid sequence as is further described herein.

As used throughout, the term "template" or the phrase "target nucleic acid sequence" refer to a nucleic acid template which is either naturally in a single stranded form, such as messenger RNA, or is denatured into a single stranded form, such as DNA. The target nucleic acid sequence according to the present invention can be in a crude, partially purified or purified form and may have varying degree of complexity depending on its origin. As used herein a specific target nucleic acid sequence may differ from another specific target nucleic acid sequence by even a single nucleotide, e.g., a point mutation, or by a plurality of nucleotides.

As used herein the phrase "complementary or substantially complementary" refers to sequences that may base pair under predetermined hybridization conditions of temperature and ionic strength and/or the presence of template. Specifically, "complementary or substantially complementary" refers to at least 70% complementary, still preferably, at least 80% complementary, advantageously, between 90% and 100% complementary. "Completely complementary" refers to 100% complementary.

As used herein, the term hairpin is used to describe a stem-loop intramolecular base pairing in single-stranded DNA or RNA. The hairpin or hairpin loop is formed from two regions of the same probe that are at least substantially complementary to each other. In the nucleotide sequence, complementary sequences base-pair to form a double helix "stem" that ends in an unpaired loop.

As used herein the phrase "thermophilic restriction enzymes" are restriction endonucleases that recognize and cleave specific nucleic acid sequences. Thermophilic restriction enzymes are less susceptible to heat. Such enzymes have a reaction temperature that is about 50° C. or higher. One example of a suitable thermophilic restriction endonuclease is BsoB1 restriction endonuclease. These enzymes cleave restriction endonuclease restriction sites (RERS). Such restriction sites are described in U.S. Pat. No. 6,743,582, U.S. Pat. No. 5,846,726 and U.S. Pat. No. 5,919,630, which are all incorporated by reference herein. BsoB1 will cleave sequences with some degree of degeneracy (i.e. variation). The degenerate sequences cleaved by BsoB1 are well known and include ctcgag, cccgag, cccggg and ctcggg. These RERS sequences are not cleaved by the enzyme when in single stranded form. However, when the RERS sequence is hybridized to its complement, it is cleavable by the restriction endonuclease. The degree of complementarity required will vary somewhat depending upon the specific RERS. However, generally, for the six base pair restriction sites, it is preferred that there is no mismatch in the site (although BsoBI, for example, can have mismatches provided that they are not at the 1, 3, 4 or 6 positions). In those instances where one of the cleavable RERS sequences is chemically modified, only the chemically unmodified RERS sequence is cleaved in the presence of the enzyme. BsoBI is an example of a restriction enzyme that can recognize a hemimodified RERS and which is capable of cleaving the unmodified strand, although other enzymes with these properties are known, including, but not limited to, Hinc II, Ava I, Nci I and Fnu 4H.

Modified restriction site probes are contemplated for use in the present invention. By introducing a modification at the recognition site of one strand of the hybridized probe, enzymatic cleavage of the modified strand can be prevented. One example of such a modification is a thioate modification that is introduced on the probe sequence complementary to the RERS sequence cleaved by the restriction endonuclease. As a result of the modification, only one strand of the restriction site will be cleaved. This is important in the context of the present invention where probes are used in multiple cycles. This approach benefits from a higher concentration of the reactants throughout the incubation and as such results in a higher efficiency of product formation. The skilled person is aware of many chemically modified restriction sites, and such are not described in detail herein. The skilled person understands that not all restriction sites are susceptible to chemical modification that will result in single strand nicking. As such only the RERS sequences for certain enzymes can be chemically modified to effect the single stranded nicking described herein.

In certain embodiments of the present invention, the chemically modified restriction site is part of a recycled probe. Certain embodiments contemplate recycling probes to further amplify signal that results from the detection of a target sequence. Once the target/probe complex denatures, then the uncleaved probe is recycled for additional use. Similar to the first generation of paired probes, the restriction endonuclease recognizes and cleaves the full restriction site (5' - - - 3') only when the two members of the paired probe hybridize to form the double stranded restriction site. However, again, only the unmodified strand of the pair of hybridized probes is cleaved. The melting temperatures of the probes (at the selected reaction temperature) are selected so that, when the chemically unmodified probe is cleaved, at least the cleaved probe denatures from its complex. In other embodiments, nicking of the single stranded chemically unmodified restriction site causes all probes to denature from the target.

In some embodiments, to enable detection, the oligonucleotide probe assemblies of the present invention are preferably tagged with a detection moiety or moieties. It will be appreciated however, and it is further detailed hereinbelow, that detection according to the present invention can also be effected without the incorporation of such detection moieties onto the oligonucleotide(s) that bind to the target. Rather, binding to target yields a probe fragment that binds to a non-target specific reporter probe, and the reporter probe hybridizes to this probe fragment.

As detailed herein, the detection of a probe and of restriction products thereof is effected using any conventional detection mechanism. For example, a fluorescent reporter dye and a quencher group which flank the restriction site of the same strand can be used. The quencher is capable of capturing the energy emitted by the fluorescent group, and as such, as long as the two groups are close enough to each other, no fluorescence will be emitted when the fluorescent group is excited. The skilled person is well aware of the considerations for configuring probes having both a quenching and a signaling moiety (in which the signal from the signaling moiety is quenched when in a certain proximity to the quenching moiety and emits signal when the spacing is increased) or probes that have two signaling moieties (where signal diminishes or ceases when distance is increased). To keep the quencher moiety in adequate proximity to the signaling moiety, the probe can be configured as a hairpin. In this structure, the folded portion of the sequence brings the quencher moiety closer to the signaling moiety than it would be if the sequence were not so folded. In such a configuration, the signaling moiety can emit signal when the hairpin denatures, thus separating the quenching moiety from the signaling moiety. If the probe has a RERS sequence, the restriction endonuclease cleaves the RERS, liberating the portion of the probe with the quencher moiety from the portion of the probe with the signaling moiety. This further separates the quenching moiety from the signaling moiety thus allowing even more signal to emit from the signaling moiety. The skilled person is aware of the amount of separation needed to achieve both quenching of signal and emission of signal. If a RERS sequence is deployed, typically a spacer of 4-18 bases is needed between the fluorescent reporter dye and a quencher group, depending on the restriction enzyme being used. Upon enzymatic cleavage, the fluorescent reporter dye and a quencher group separate from each other and become dispersed in solution. As a consequence, the energy transfer from the fluorescent group to the quencher does not exist, and fluorescence may be detected.

Since fluorescence may be detected as the reaction proceeds, a real-time measurement of the amplification is possible. The intensity and rate of fluorescence increase, may allow estimation of the number of target molecules present in the mixture and the rate of amplification.

As noted above, many fluorescent/quencher or donor/acceptor combinations may be utilized by the probes of the present invention. Combinations in which the donor is from the xanthene group of dyes, including fluoresceins, and the quencher is from the rhodamine group of dyes (6-FAM and TAMRA, for example) are commonly used in the art. Cy5 and ROX is another pair of dyes that can be used. When two signaling moieties are employed such as, for example, a fluorescein/rhodamine pair, the fluorescein donor is excited and transfers energy to the rhodamine acceptor which emits fluorescence at a characteristic wavelength, thereby enabling detection. If the distance between the fluorescein and the rhodamine increases, then diminished or no signal is detected.

Non-fluorescent quenchers such as DABCYL and QSF-7 can also be used; these quenchers allow a higher degree of flexibility in choosing the fluorescent dyes. The choice of dye-pair requires that the quencher will absorb the energy of the fluorescent dye when the two are in close proximity. It is preferable that the increase in fluorescence upon dye separation would be as large as possible (3-20 fold increase in fluorescence was reported for various energy transfer systems). When only one fluorescent dye is used, a dye with the highest fluorescence intensity (usually having a broad emission spectrum) should be chosen. If two probes that carry the same fluorescent/quencher groups are designed for the detection of two distinct regions of the same target, sensitivity of the assay may be increased. Alternatively, two or more probes that are targeted to different targets can also be used providing that different combinations of fluorescent/quencher dyes are utilized. However, in case when two or more fluorescent dyes are used, the sensitivity of the assay may be compromised in order to distinguish among the fluorescence of the various dyes. This may be done by detection of narrower emission spectrums, in which the fluorescence of the various dyes would not overlap.

The following paragraphs describe oligonucleotide probes which are taught by the prior art yet are used in accordance with the teachings of the present invention with certain restrictions to be further emphasized below, which restrictions result in far superior detection of target nucleic acids due to signal amplification and/or reduction of background signal.

FIG. 1A illustrates a first embodiment for using target specific probes 10 and 20 where the imaging moiety is specific for the target. In FIG. 1A, sequences represented by (a) and (e) are specific for the target sequences (a') and (e'). Sequences (c) and (c') are selected to provide a restriction site for a thermophilic restriction enzyme. One example of a thermophilic restriction endonuclease is BsoB1.

Figure 1B:
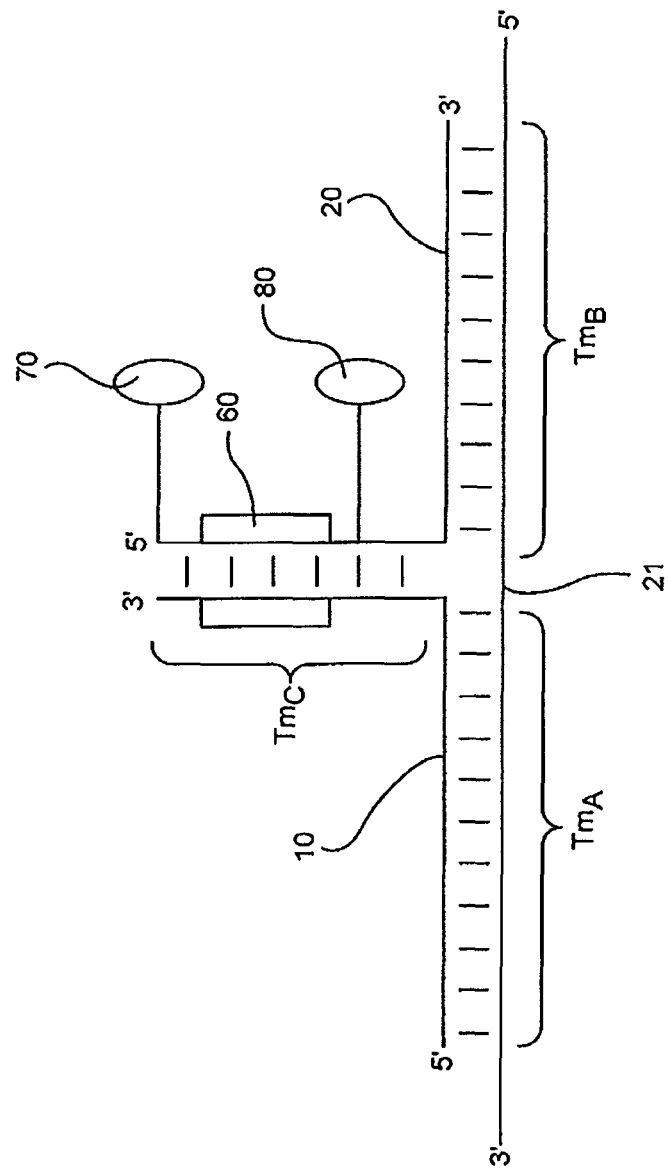

FIG. 1B illustrates a complex formed from the probes 10 and 20 illustrated schematically in FIG. 1A. Probes 10 and 20 hybridize to their respective target sequences (a') and (e') at a reaction temperature ($T_{Hyb}$) that is less than the melting temperature of probe 10 coupled to the target 21 ($T_{mA}$) or the melting temperature of probe 20 coupled to the target ($T_{mB}$). Because of the fact that $T_{Hyb}$ is greater than at least one of $T_{mA}$ or $T_{mB}$, probes 10 and/or 20 cycle on and off the target as the probe:target complexes form and at least one of the probes 10 or 20 is cleaved, causing the probes to denature from the target 21 or target/probe complex. In some embodiments, this probe cycling is accomplished and/or accompanied by temperature cycling. This probe cycling facilitates signal amplification by allowing more probes to hybridize to the target. The skilled person is aware that the melting/hybridization temperatures are a function of length and composition of the sequences. The skilled person can select a sequence length and sequence composition that is suitable for use at a given $T_{HYB}$.

In this embodiment, the thermodynamic relationship between the melting temperatures of the three hybridized portions of the complex and the hybridization temperature is: $T_{mC} < [T_{mA}$ or $T_{mB}] < T_{Hyb}$ (where $T_{mC}$ is the melting temperature of the hybrid formed between regions (b c d) and (b' c' d') of probes 10 and 20, respectively). This relationship prevents the formation of Probe 10: Probe 20 complexes in solution in the absence of the target nucleic acid sequence. In a preferred embodiment, the sequences are selected to provide a complex with base stacking. One skilled in the art is aware of the manner in which base stacking will contribute to the stability of the complex illustrated in FIG. 1B.

Hybridization of (a) and (e) to their respective targets brings the complementary regions (b) and (b'), (c) and (C') and (d) and (d') into close proximity, increasing their local concentration such that hybridization occurs to form a ternary complex which possesses a double stranded restriction site 60. This newly formed restriction site 60 is then cleaved by the appropriate enzyme (e.g. BsoB1) to separate the fluorophore 70 from the quencher 80 which generates fluorescence in a target-dependent manner.

In a preferred embodiment, the melting temperatures $T_m$ of (a):(a') or (e):(e') are higher than that of (b, c, d):(b', c', d'). The reaction is conducted at an elevated temperature $T_{Hyb}$ to prevent target-independent formation of (b, c, d):(b', c', d') duplexes. In this embodiment, the restriction enzyme is also thermophilic to ensure maintenance of enyzymatic activity over the course of the reaction.

Stacking of paired bases in hybridized regions (a):(a') and (e):(e') may also enhance the stability of the tertiary probe: target complex. Stacking of paired bases is described in Lane, M, et al, "The thermodynamic advantage of DNA oligonucleotide 'stacking hybridization' reactions: energetics of a DNA nick," *Nucleic Acids Research* Vol. 25, No. (1997); Yakovchuk et al., "Base-stacking and base-pairing contributes into thermal stability of the DNA double helix," *Nucleic Acids Research*, Vol. 34, pp. 564-574 (2006); Zhu, L., et al, "Development of a base stacking hybridization-based microarray method for rapid identification of clinical isolates," *Diagnostic Microbiology and Infectious Disease*, Vol. 59, pp. 149-156 (2007) all of which are incorporated by reference. Optionally, in multiplexed reactions, the sequences of regions (b-d) and (b'-d') are specific to each probe pair to reduce potential for target-independent hybridization of Probes 10 and 20 among the various sets of probes in the multiplexed reaction. One or both of Probe 20 and labeled Probe 10 can be configured with a hairpin structure that will prevent the two probes from target-independent hybridization. However, given the slow kinetics of signal amplification achievable with this embodiment as discussed in further detail below, configuring the probes with a hairpin structure will restrict the use even further.

One disadvantage to the embodiment illustrated in FIG. 1A-B is the rate at which probes 10 and 20 cycle on and off the target. In this embodiment, accumulation of fluorescence is dependent upon dissociation of cleaved probe from the target and hybridization of Probes 10 and 20 to the target to form additional complexes. Comparing this embodiment to Strand Displacement Amplification (SDA), in SDA, the doubling time is approximately 30 sec (see Spargo, et al., "detection of *M. tuberculosis* DNA using thermophilic strand displacement amplification," *Mol. Cellular Probes*, Vol. 10, pp. 247-256 (1996)) and detection of amplified target in a real-time fluorescence-based system requires accumulation of about $10^8$ cleaved probe molecules. From an input level of $10^3$ target molecules, $10^5$-fold amplification is therefore required (assuming that each copy of target leads to cleavage of one probe molecule), taking approximately log $10^5$ cycles (doublings) divided by log 2 or roughly 16.6×30 sec=8.5 min. By contrast, in the embodiment illustrated in FIGS. 1A-B, assuming a cycle time of about 3 seconds (i.e., 1/10th that of SDA), the time required to generate $10^8$ cleaved probes from $10^3$ copies of target is given by: $10^8 \div 10^3 \times 3$ sec=300,000 sec=83.3 h, which is an unacceptable length of time for most applications.

In preferred embodiments, a secondary, self-sustaining means of probe cleavage increases the rate of accumulation of cleaved probes. These embodiments provide a mechanism that triggers probe cleavage. In these embodiments, the target and, in certain embodiments, one or more of the probes are continuously recycled. In certain embodiments the recycled components induce additional rounds of probe cleavage without the need for additional analyte-specific hybridization events.

Figure 2A:
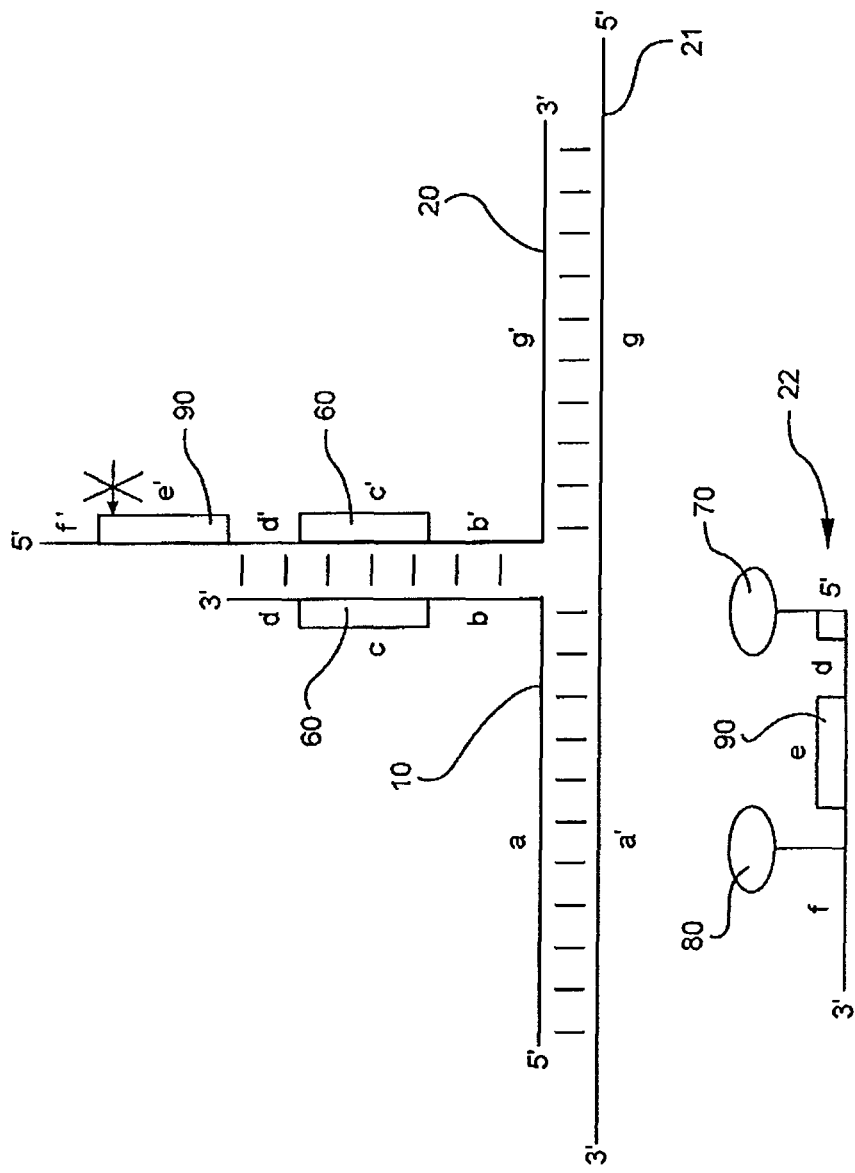
FIGS. 2A-2C illustrate a method that utilizes three probes, one of which a non-target specific labeled reporter probe, but wherein the probes do not possess secondary structure when unbound to target.
Figure 2B:
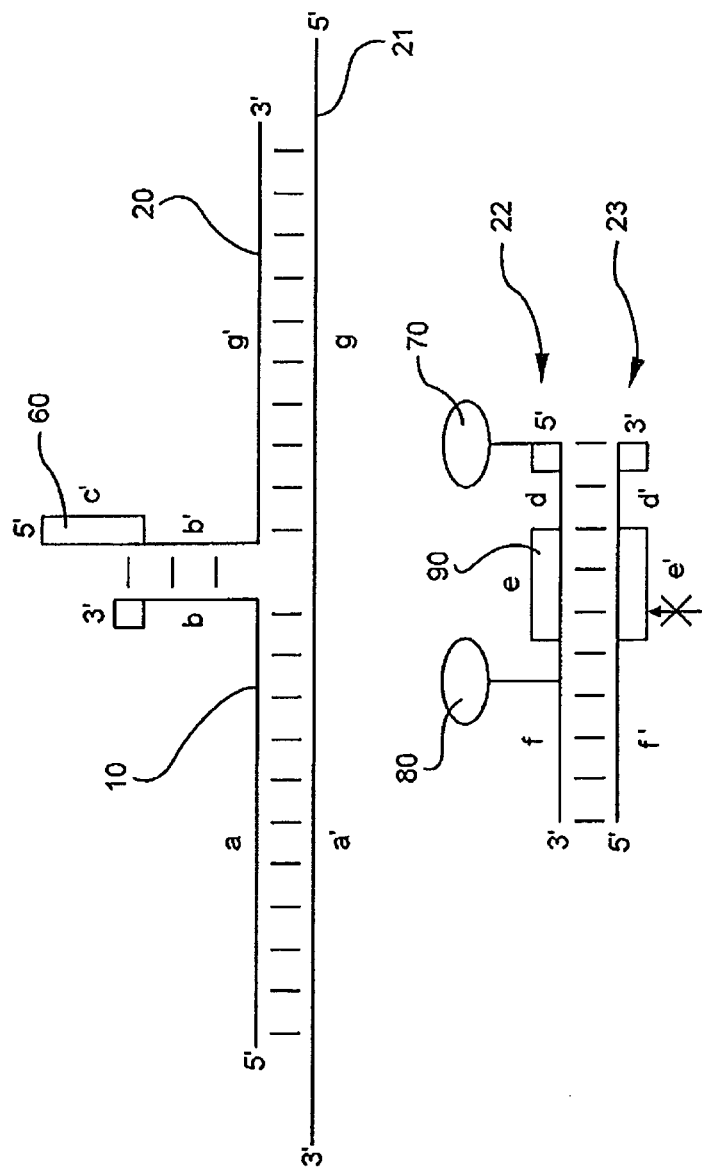
Figure 2C:
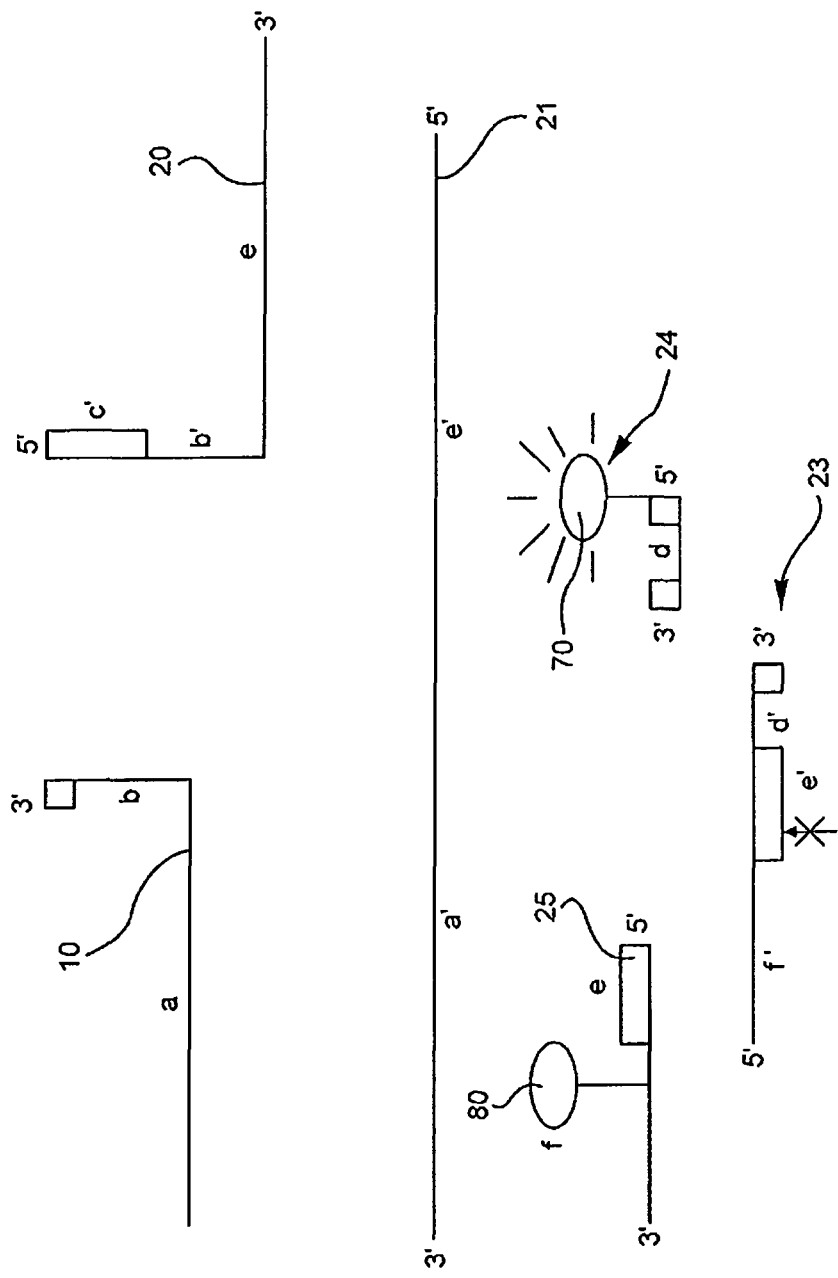

Self-sustaining probe cleavage is illustrated in FIGS. 2A-2C. In this embodiment there are three Probes, Probe 10, Probe 20 and Probe 22. Probe 10 has a first sequence (a) that is the complement of a sequence (a') on the target nucleic acid. Probe 10 also has sequences (b, c and d) that will hybridize to sequences b', c' and d' on Probe 20.

In FIG. 2A, neither Probe 10 nor Probe 20 is provided with a reporter (fluorophore 70 and quencher 80 as illustrated in FIGS. 1A and 1B). Instead, Probe 20 is provided with a sequence (e') that will hybridize to a complementary sequence (e) on the non-specific labeled reporter probe 22.

FIGS. 2A-C illustrate a Probe 20 that is modified to comprise a 5' tail with two BsoBI restriction sites, one of which is thioated to prevent cleavage. To minimize target independent hybridization of Probes 10 and 20 with their complementary sequences ((b, c, d):(b', c', d')), the reaction is carried out at a high temperature $T_{Hyb}$, that is at or above the melting temperatures T, of the target-specific probe regions (a) and (g').

Hybridization of (a) in Probe 10 and (g') in Probe 20 to their complementary target sequences (a' and g) in the target brings regions (b, c, d) of Probe 10 and (b', c', d') of Probe 20 into close proximity, leading in turn to their hybridization and formation of a double stranded restriction site 60. The restriction site 60 is cleaved by the BsoBI enzyme to release a single stranded fragment 23 from Probe 20 (d', e', f') that does not have a complement in Probe 10. The Probe 20 fragment 23 (d', e', f') is complementary to the sequence of labeled Reporter Probe 22(*d, e, f*). Hybrization of fragment (d', e', f') to the Reporter Probe 22 leads to formation of a hemithioated BsoBI restriction site 90 as illustrated in FIG. 2B. The unmodified (labeled) strand of this duplex is nicked by the BsoBI enzyme to produce fragments 24(*d*) and 25(*e, f*) as illustrated in FIG. 2C that dissociate from their complementary sequences, thereby separating the fluorophore 70 and quencher 80 and generating fluorescence in a target-dependent manner. An important aspect of this embodiment is the ability of the thioated DNA strand (f', d', e') to undergo further rounds of probe hybridization and single stranded nicking, thereby leading to the accumulation of fluorescence, independent of further analyte-specific probe hybridization. For multiplexed applications in which more than one target analyte is detected, reporter Probe 22 may comprise a universal sequence that is complementary to the 5' tails of multiple analyte-specific Probe 20 sequences. That is, multiple different target specific Probe 20'*s* will have the identical sequence (f', e', d') at their 5' tails.

Although the mechanism described in FIGS. 2A-2C is useful as a pedagogic tool to describe the concepts of the present invention, this mechanism provides the possibility of target-independent signal due to hybridization of (b, c, d) to (b', c', d') in solution in the absence of sequences complementary to regions (a) and (g') (i.e. in the absence of target). Once this complex is formed, the restriction site is cleaved, which generates the fragment (d', e', f') independently from the presence of the target, which yields a false positive.

Figure 3A:
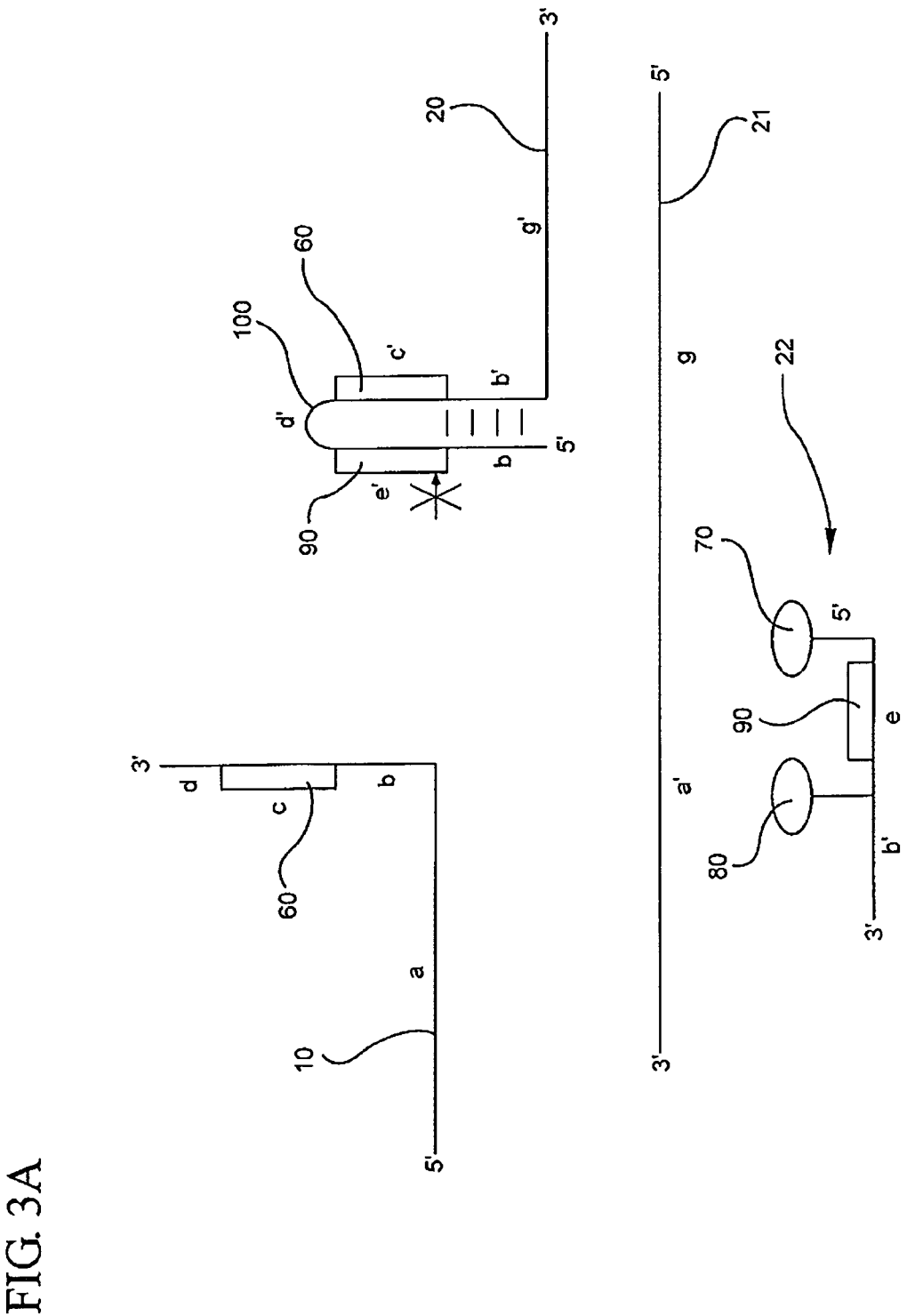
FIGS. 3A-3D illustrate a third embodiment of the present invention that utilizes three probes wherein one target specific probe is equipped with a hairpin structure to block target independent hybridization between the target-specific probes.
Figure 3B:
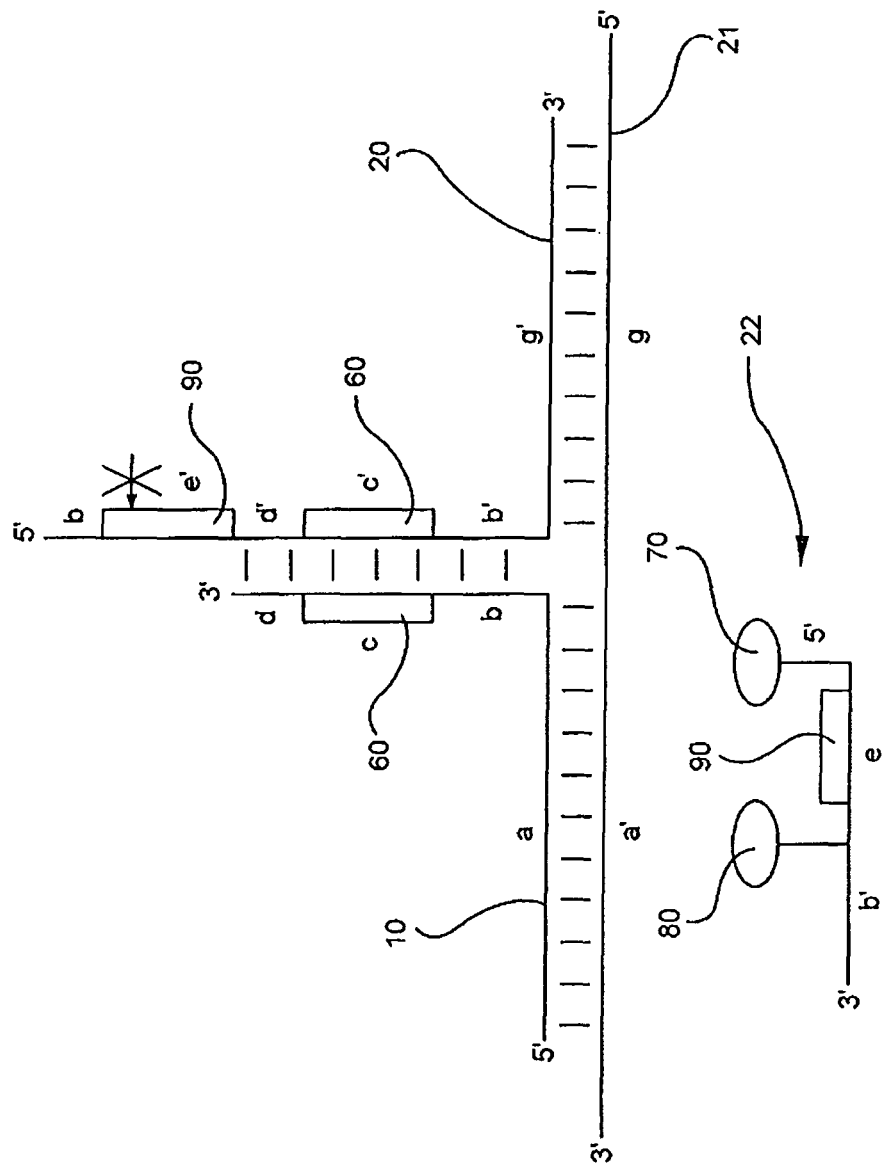
Figure 3C:
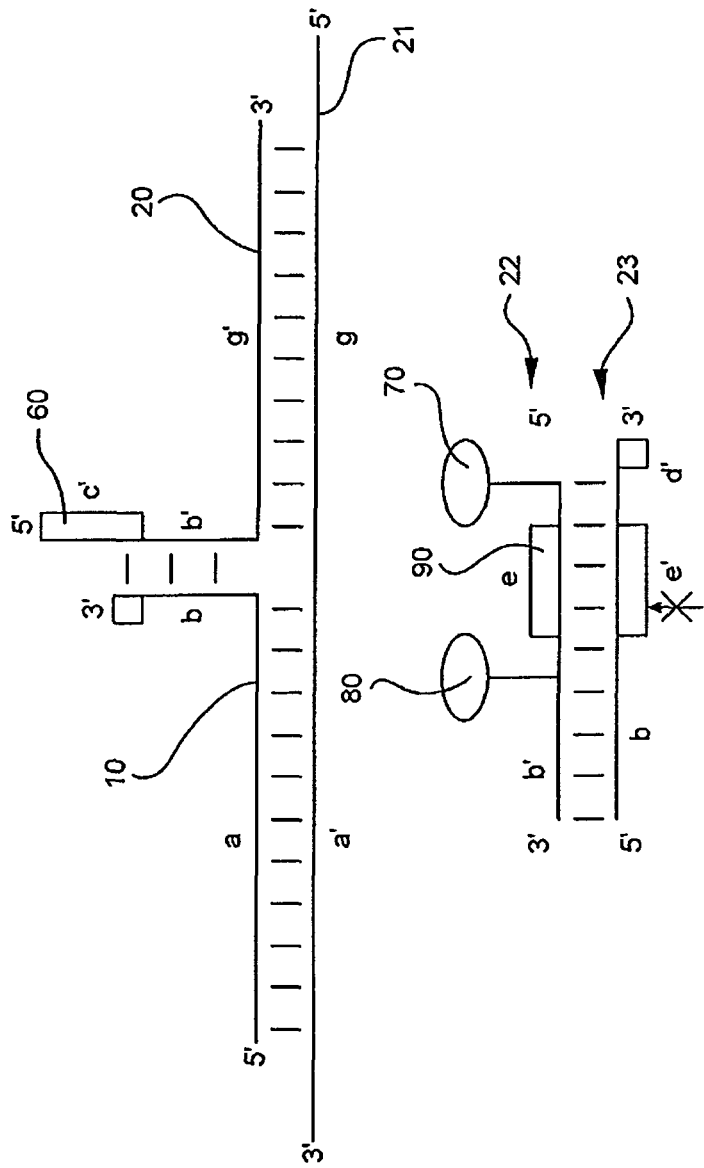

A second embodiment mitigates the potential for target-independent signal and is illustrated in FIGS. 3A-D. In this embodiment, Probe 20 is configured to have a stable hairpin structure 100. The hairpin 100 blocks hybridization to the 3' tail of Probe 10 when the two probes are free in solution. Note that the hairpin structure has two RERS sequences, 60 and 90. Since these RERS sequences are located at least partially within the loop of the hairpin structure and are preferably configured to be degenerate recognition sequences for the same restriction endonuclease, they do not form a double stranded restriction, site that is susceptible to being cleaved by the restriction enzyme. When the two probes 10, 20 are brought together through hybridization of their respective regions, (a) and (g'), to their respective target sequences, (a') and (g), conditions are such that that double stranded hairpin is denatured. Referring to FIG. 3B, when Probes 10 and 20 are hybridized to the specific target, the local concentrations of the two complementary tail sequences of Probe 10 (i.e. sequences b, c, d) and 20 (i.e. sequences b', c', d') are sufficiently high such that intermolecular hybridization of (b, c, d):(b', c', d') occurs. Note that, in the configuration illustrated in FIG. 3A, Probes 10 and 20 both have a sequence b. The complement of sequence b, denoted (b') is in Probe 22. The hairpin structure 100 keeps Probe 20 that is free in solution and not hybridized to the target from binding to the Universal Labeled Reporter Probe 22. Probe 10 and Probe 22 have respective complementary sequences (b, c, d and b', c', d') but are otherwise configured to not hybridize when both are free in solution. In an alternative embodiment, Probe 10 also has a hairpin. Once Probes 10 and 20 are brought into proximity due to their binding to the target, hybridization of (b, c, d) in Probe 10 to (b', c', d') in Probe 20 occurs. This is illustrated in FIG. 3B. Hybridization produces a double stranded recognition site 60 that is cleaved by the restriction enzyme (BsoB1) to generate fragment 23 (d', e', b) that is complementary to (b', e) in Labeled Reporter Probe 22.

Figure 3D:
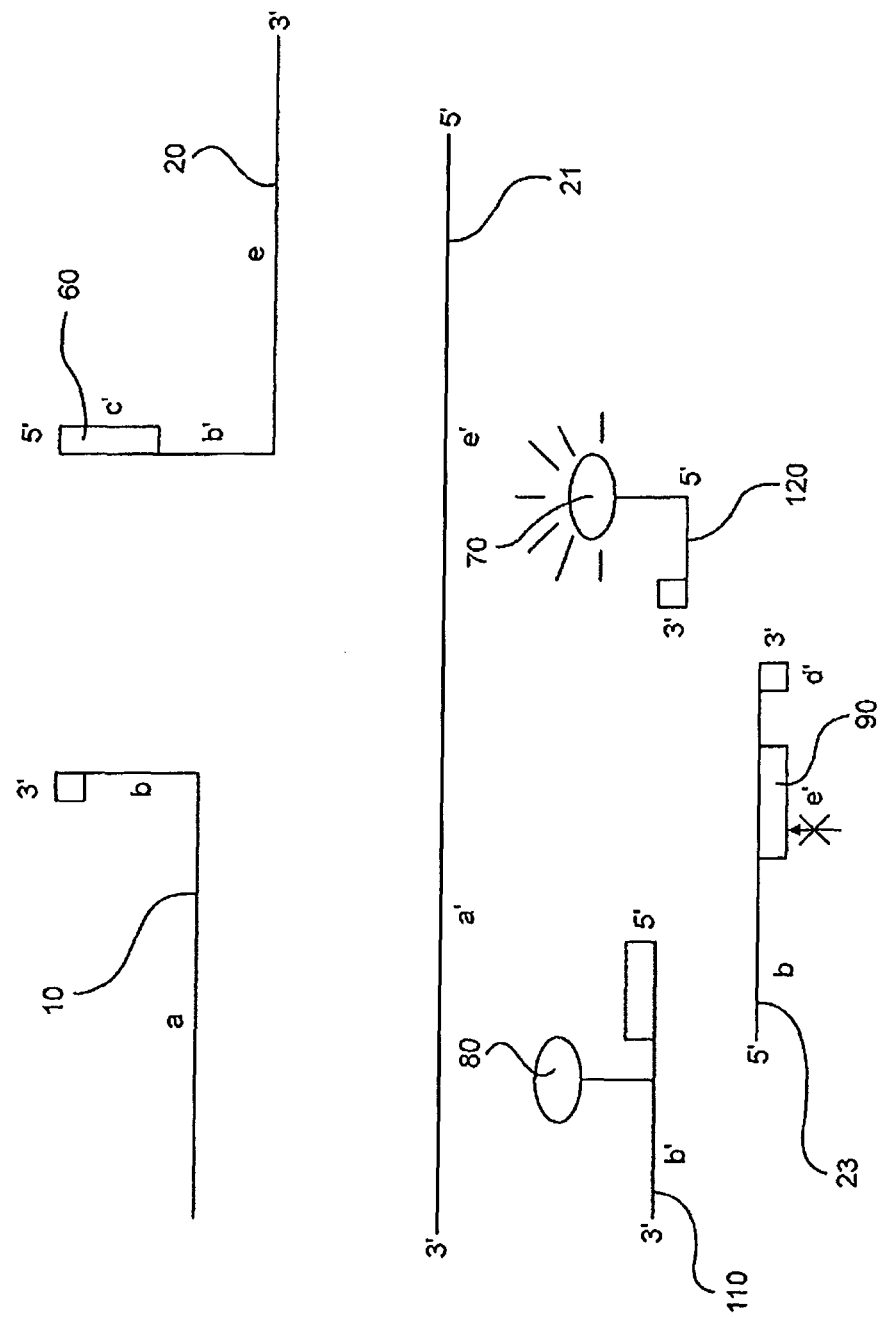

Hybridization of Probe 20 fragment 23 (d', e', b) to Probe 22 creates a double stranded hemithioated restriction site 90, which is nicked by the restriction enzyme on the strand corresponding to Probe 22. Referring to FIG. 3D, one nicked fragment 110 has sequence (b') and the quencher moiety 80.

One example of a quencher moiety 80 is Dabcyl. However, this is but one example and the skilled person is aware of many suitable quencher moieties as previously noted. The other nicked fragment 120 of Reporter Probe 22 carries the fluorescence moiety 70 (e.g. a fluorophore).

Dissociation of the nicked fragments 110, 120 of the Reporter Probe 22 from their complementary fragment 23 (b, e', d') of Probe 20 and from each other leads to generation of fluorescence and regeneration of single stranded Probe B fragment 23 (b, e', d'). The protected (e.g. thioated) single stranded fragment of DNA 23 can then undergo further rounds of self-regenerating probe hybridization and single stranded cleavage, leading to the accumulation (and amplification) of fluorescent signal.

Referring to FIGS. 4A-4D, an unlabeled hairpin probe 200 is used as an intermediary in the generation of target-specific fluorescence. Probe 200 has a first sequence (b'-i') that is the complement of a portion of the target sequence 201 ($b-i$). Probe 200 has a second sequence (a-c') with a portion (d-e) that is a single stranded thioated portion of a restriction site 205. Note that a portion of the first sequence (b'-i') and all of the second sequence (a-c') of the first oligonucleotide probe 200 form a hairpin structure. Since the hairpin includes a portion of the Probe 200 sequence that binds to the target binding sequence, hybridization of Probe 200 to target 201 causes the hairpin of Probe 200 to denature (i.e. become unhybridized). The single stranded thioated restriction site is not digested (i.e. nicked) by restriction endonuclease.

Figure 4A:
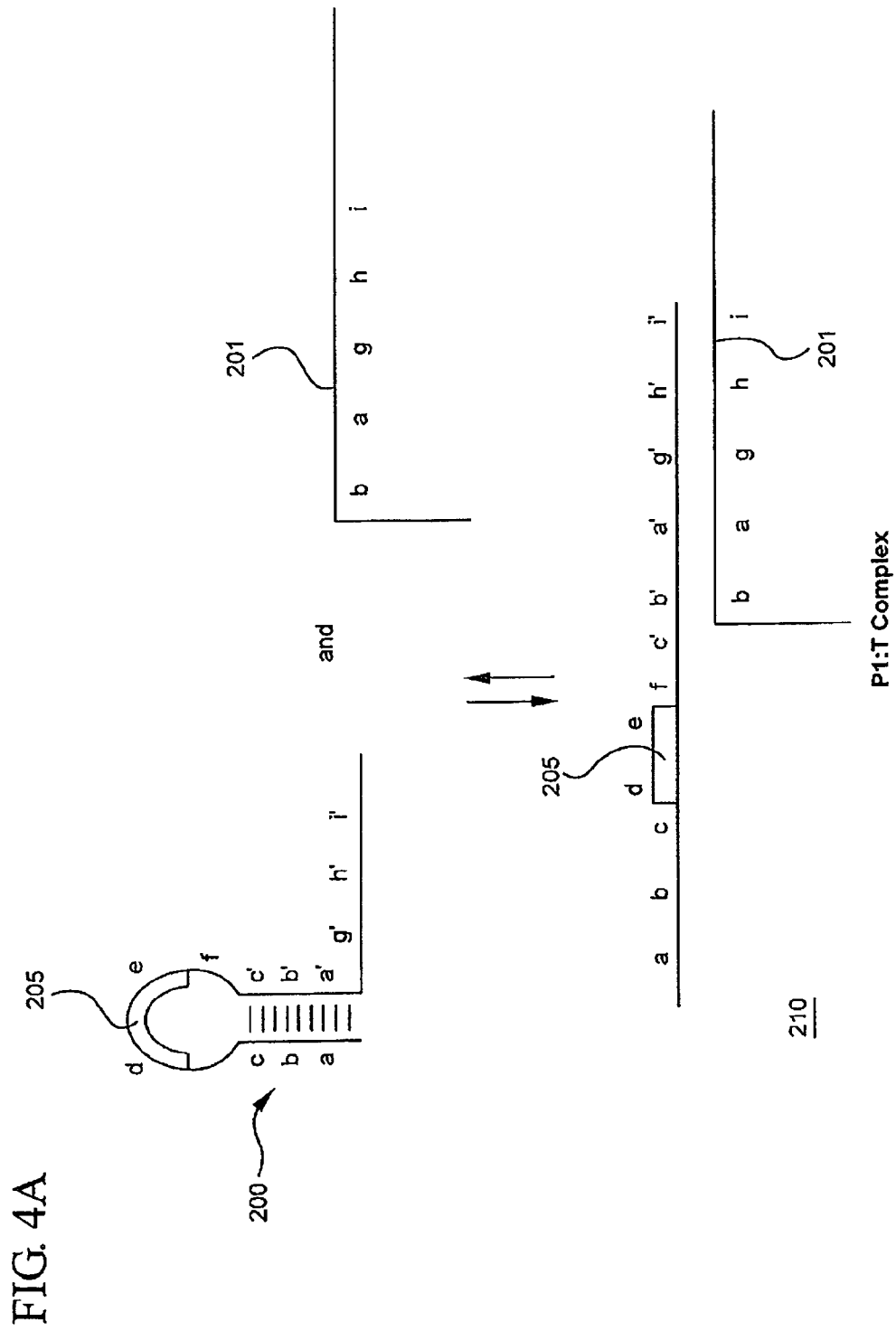
FIGS. 4A-4D illustrate a fourth embodiment wherein only one probe is target specific.
Figure 4B:
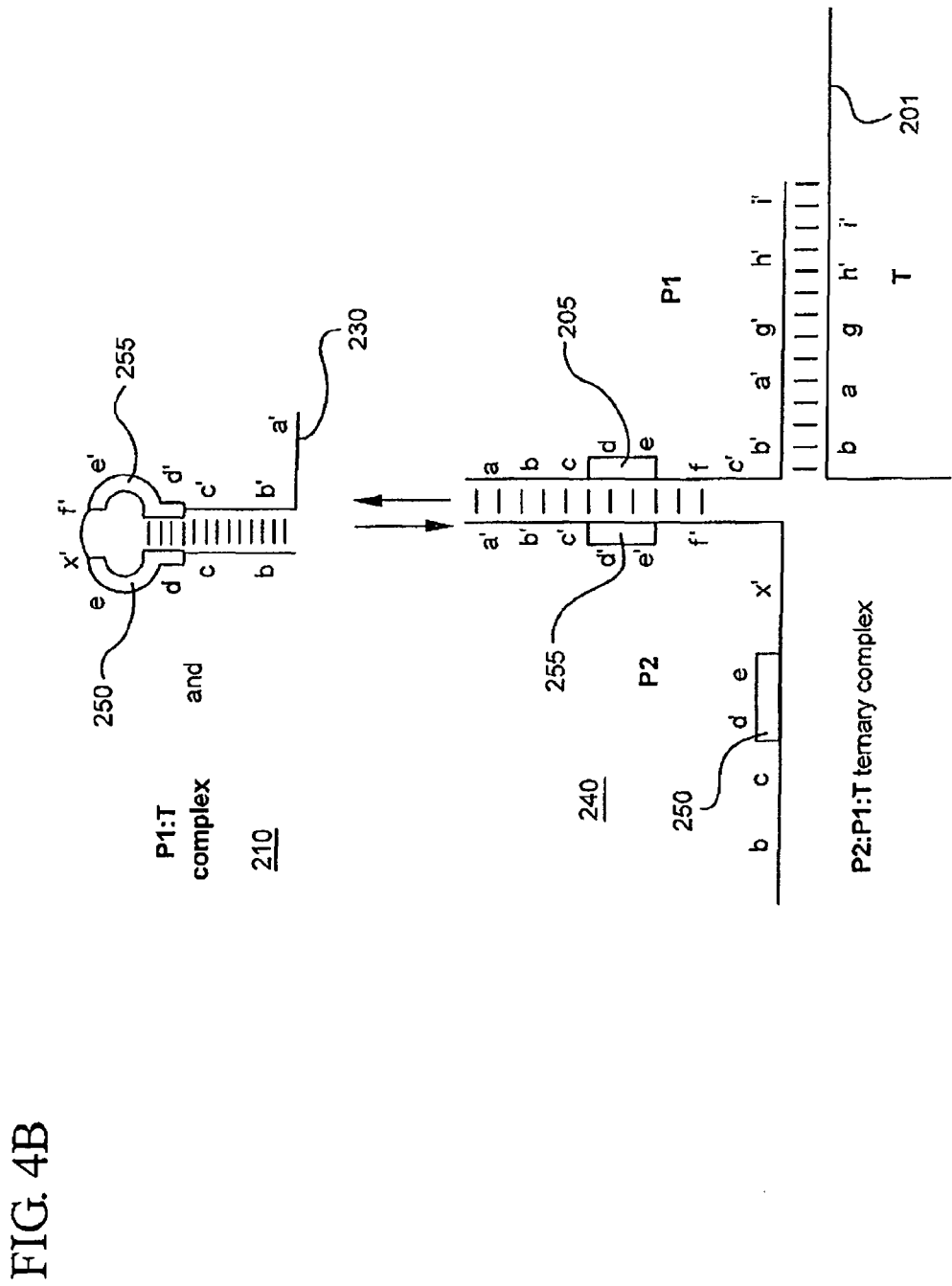
Figure 4C:
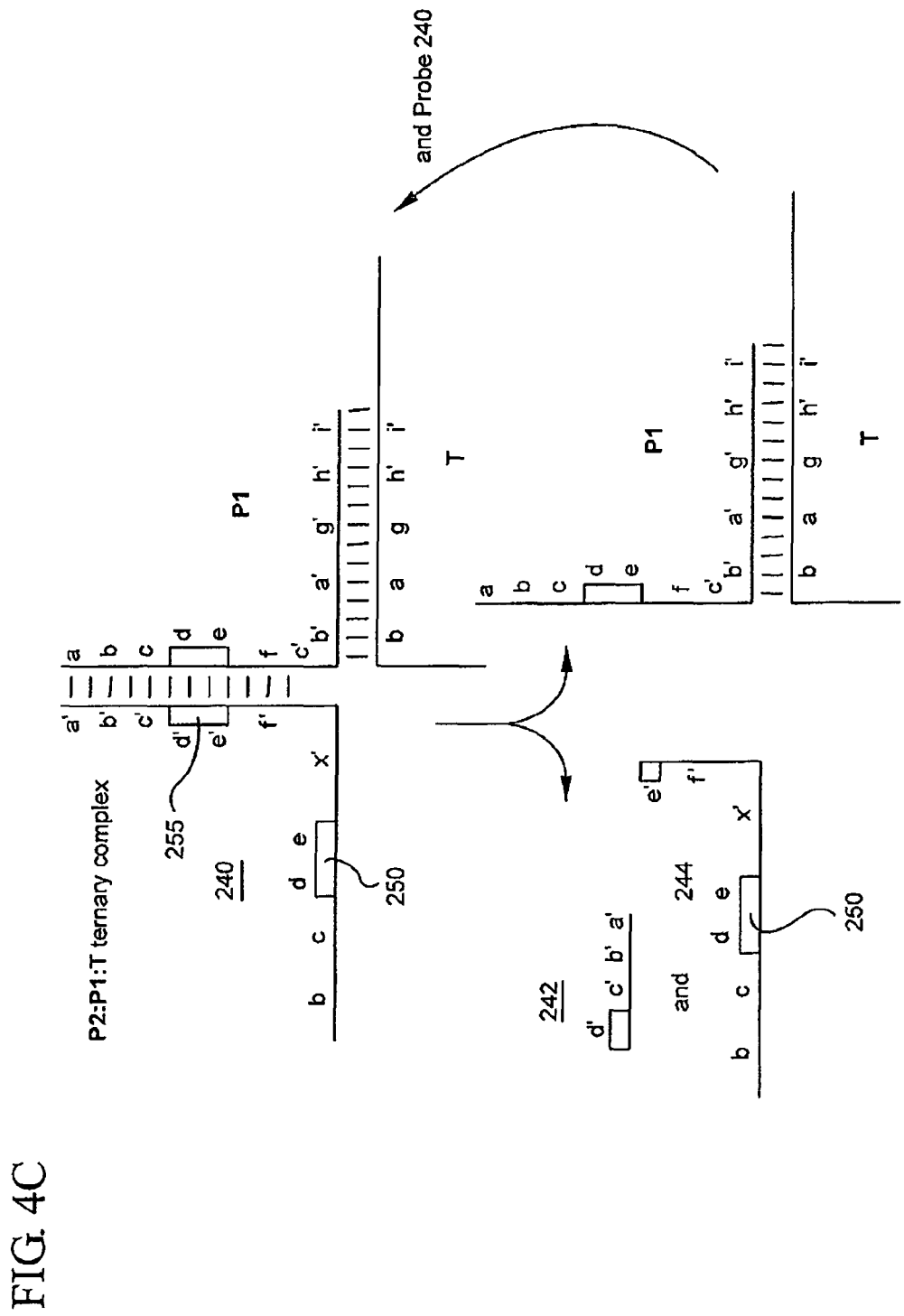
Figure 4D:
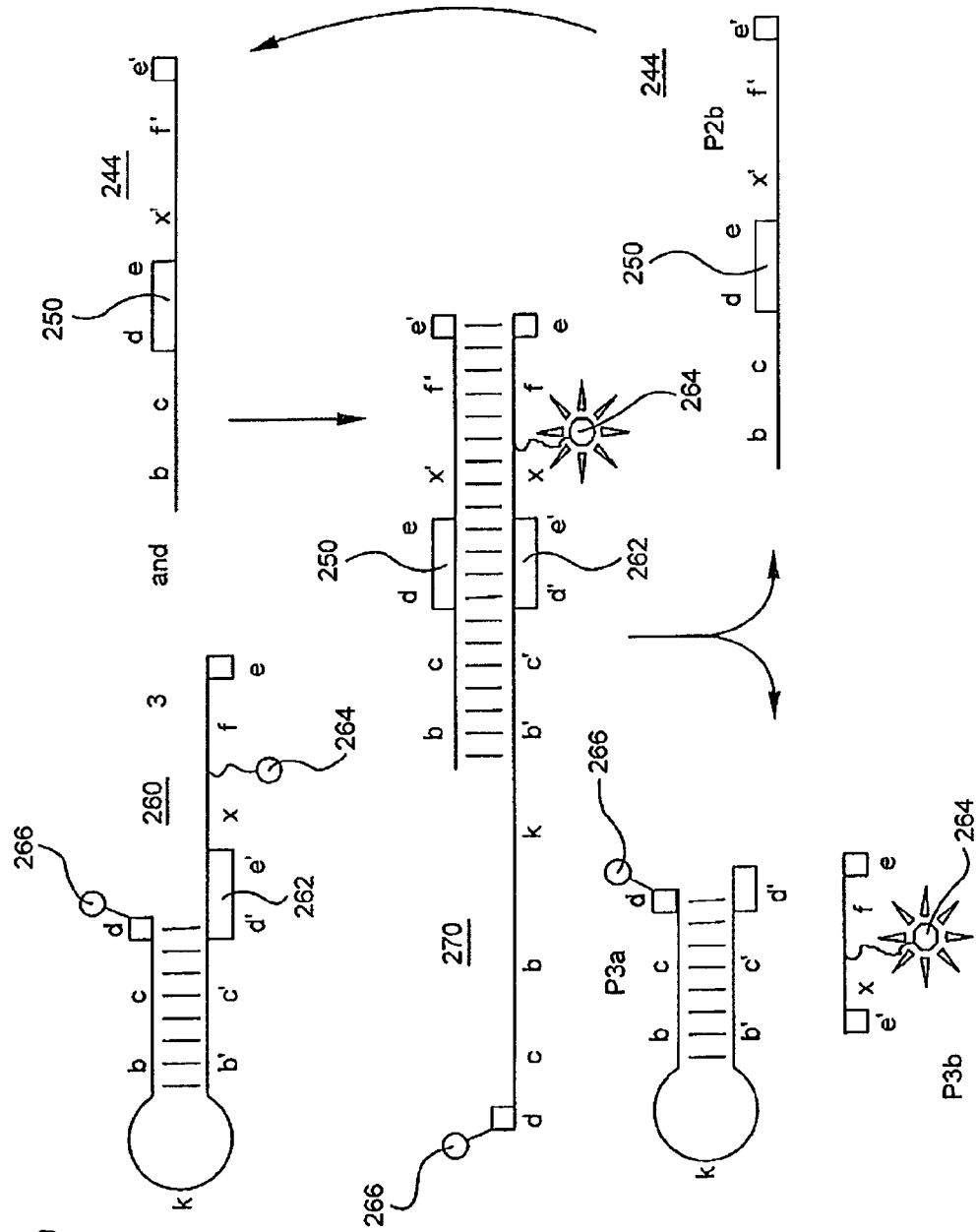

Probe 200 hybridizes to the complementary target and forms the more thermodynamically stable heteroduplex complex 210. Referring to FIG. 4B, complex 210 is hybridized to hairpin Probe 230. Hairpin Probe 230 has a first sequence (a'-f') that will hybridize to sequence (a-f) of complex 210. Probe 230 has a second sequence (b-e') that is complementary with and hybridizes to a first sequence (b'-e) on the third oligonucleotide probe 260 (FIG. 4D). Note that both first and second sequences include e' and f'. Note that x' is intermediate e and f'. All of the first sequence and part of the second sequence form the hairpin structure (b-b') of the second oligonucleotide Probe 230. A portion 255 (d', e') of the first sequence (a'-f') of Probe 230 forms a restriction site with a portion 205 ($d, e$) of the second sequence (c'-a) of Probe 200 in complex 240. A portion 250 ($d-e$) of the second sequence (b-e') of probe 230 forms a hemi-thioated restriction site with a portion 262 (d'-e') of the first sequence (b'-e) of Probe 260 (FIG. 4D). Note that, in Probe 260, x is intermediate e' and f. x is complementary to x' in hairpin probe 230.

Hybridization of Probe 230 forms the thermodynamically favored ternary structure 240 (Probe 230:Probe 200:target 201). Probe 230 carries both a protected (e.g. thioated) restriction site 250 and an unprotected (e.g. unthioated) restriction site 255. Referring to FIG. 4C, nicking of the unprotected strand 255 of the restriction site leads to formation of sub-fragments 242($d'$-a') and 244(b-e') that dissociate from Probe 200.

The fragment 244 ($b$-$e'$) is complementary to the first sequence (b'-e) of the labeled hairpin Reporter Probe, 260, as shown in FIG. 4D. Due to the length of their complementary sequences, hybridization of 244 to Probe 260 is thermodynamically favored over maintenance of the Probe 260 hairpin structure. As a result, the intramolecular base pairing in Probe 260 is disrupted, which leads to the formation of a complex 270 (Probe 260:sub-fragment 244). Probe 260 also has a signaling moiety 264 (e.g. a fluorophore) and a quenching moiety 266. The disruption in intramolecular base pairing in Probe 260 separates the signaling moiety 264 from the quenching moiety 266 and an increase in signal results. The unprotected restriction site 262 (d'-e') is then nicked by the restriction endonuclease further separating the fluorophore 264 (attached to P3b) and quencher 266 (attached to P3a), which leads to a further increase in fluorescence. The P2b fragment 244 ($b$-$e'$) denatures from the cleaved portions (P3a and P3b) of Probe 260 and is free to bind to another Probe 260, where the cycle of i) hybridization to form complex 270; ii) cleavage of the unprotected strand (d'-e') of the hemi-thioated duplex restriction site; and release of Probe 230 fragment 244 is repeated.

FIG. 5 is one embodiment of specific SEQ ID's for Probes 200, 230 and 260 for use in the embodiment illustrated in FIGS. 4A-D. Probe 200 is a 58-mer specific for an HPV 16 target. The Probe 200 is SEQ ID NO. 1. The HPV 16 target is SEQ ID NO: 2. The target sequence for HPV-16 is illustrated in FIG. 7A. The HPV 16 sequence (highlighted in bold italics) is complementary to and hybridizes to the 27 nucleotides at the 3' end of probe 200 (FIG. 5; SEQ ID NO: 1).

It is contemplated that Probe 200 will also hybridize to an HPV-58 target. The HPV-58 target is illustrated in FIG. 7B. This is SEQ ID NO: 3 in FIG. 7B. The highlighted sequences in the HPV-58 sequence contain regions of complementarity (indicated by upper case nucleotides) with 200 (FIG. 5) interspersed with 5 mismatched nucleotides designated by lower case. Calculations based on a 3-state equilibrium model (Bonnet et al Proc. Natl. Acad. Sci. 96:6171-6176 (1999)), which take into account the free energy cost for unfolding of the 200 hairpin during formation of the P1:target complex, indicate that the fraction of matched target (HPV-16) hybridized to 200 under typical reaction temperatures (~50° C.) will be approximately 10,000-fold greater than the fraction of mismatched target (HPV-58) that hybridizes. This model therefore predicts much lower signal for the mismatched (HPV-58) target relative to the matched (HPV-16) target.

Nucleotides 1-18 in Probe 200 are complementary to nucleotides 31-48 in Probe 200 and form the hairpin structure in Probe 200. The thioated RERS sequence 205 in Probe 200 is nucleotides 19 to 24 and is sequence ctcggg, which is one of the sequences susceptible to cleavage by BsoBI. However, due to its chemical modification, RERS sequence 205 is not cleaved when it forms a duplex restriction site with 255 in Probe 230. As stated above, when probe 200 is placed into proximity with the target sequence thermodynamic equilibrium favors the denaturing of the hairpin in favor of Probe 200 forming a complex with the target sequence. Probe 200 has a dG value equal to about −13.086 kcal/mole. The dG values reported herein were calculated according to Markham, N. R., and Zuker, M., "DINAMelt web server for nucleic acid melting prediction," Nucl. Acid Res. Vol. 33, pp. w577-w581 (2005), Markham, N. R. & Zuker, M. "UNAFold: software for nucleic acid folding and hybridization," Bioinformatics," Vol. II: Structure, Functions and Applications, No. 453 (Keith, J. M., ed., 2008); Methods in Molecular Biology, Ch. 1, pp. 3-31(Humana Press, Totowa, N.J. 2008). This value is the free energy of the probe's secondary structure and indicates the relative stability of the hairpin under a given set of conditions (salt concentration, temperature, DNA concentration, etc). The higher the value (more negative) the more energy required to denature the hairpin.

The skilled person is aware of the many factors that are considered in probe designs, especially in an isothermal process. Specifically, a restriction endonuclease has a defined temperature range in which it is optimally active. The restriction endonuclease is therefore selected based upon the temperature of the isothermal process. Also, probe stability is a function of temperature. Longer probes (i.e. those with more complementary nucleotides to the target sequence) will hybridize at higher temperatures than shorter probes (i.e. those with fewer complementary nucleotides). Probe composition, (i.e. the particular nucleotides that make up the sequence), will affect the melting temperatures of the probes and the hybridization temperatures. Many other factors also influence probe design and these are well known to the skilled person. In the embodiment illustrated in FIG. 5, the temperature of the isothermal process is in the range of about 55° C. to about 60° C.

Probe 230 is a 45-mer illustrated as SEQ ID NO. 4. In Probe 230, nucleotides 17 to 45 are complementary and specific for nucleotides 2 to 30 of Probe 200. Nucleotides 1 to 14 and 25-37 form the hairpin of Probe 230. Nucleotides 10 to 15 of Probe 230 are the protected RERS sequence 250 and nucleotides 23 to 28 are the unprotected RERS sequence 255. The unprotected restriction site 255 is the complement of the protected restriction site 205 on Probe 200. As previously noted RERS sequence 250 is degenerate to RERS sequence 255. As stated above, when probe 230 is placed into proximity with the complex 210 (probe 200:target sequence 201) thermodynamic equilibrium favors the denaturing of the hairpin in favor of forming the complex 240 with the complex 210. In this regard, the value of dG for Probe 230 is −10.79 kcal/mole.

The nucleotide sequence of Probe 260 (without signaling and quenching moieties) is illustrated as 40-mer SEQ ID NO. 5. Nucleotides 1 to 17 are complementary to nucleotides 7 to 23 on fragment 244 of Probe 230 and bind thereto (after Probe 230 has been nicked by restriction endonuclease to form fragments 242 and 244 that denature from complex 240). Probe 260 has a dG value of −12.059 kcal/mole. The thermodynamics are such that proximity of the probe 260 to fragment 244 from Probe 230 causes the hairpin of Probe 260 (formed by nucleotides 11-24 and their complementary sequence, nucleotides 28-40) to denature, unfolding the hairpin. Probe 260 has an unprotected RERS sequence 262 at nucleotides 9 to 14. This is complementary to and aligns with the thioated RERS sequence 250 (nucleotides 10 to 15) of fragment 244. The resulting double stranded restriction site is nicked by restriction endonuclease, creating two fragments of Probe 260. The first fragment, defined by nucleotides 1 to 9, carries the signal moiety 264 (e.g. a fluorophore). The second fragment, defined by nucleotides 10 to 40, carries the quencher moiety 266.

Figure 6:
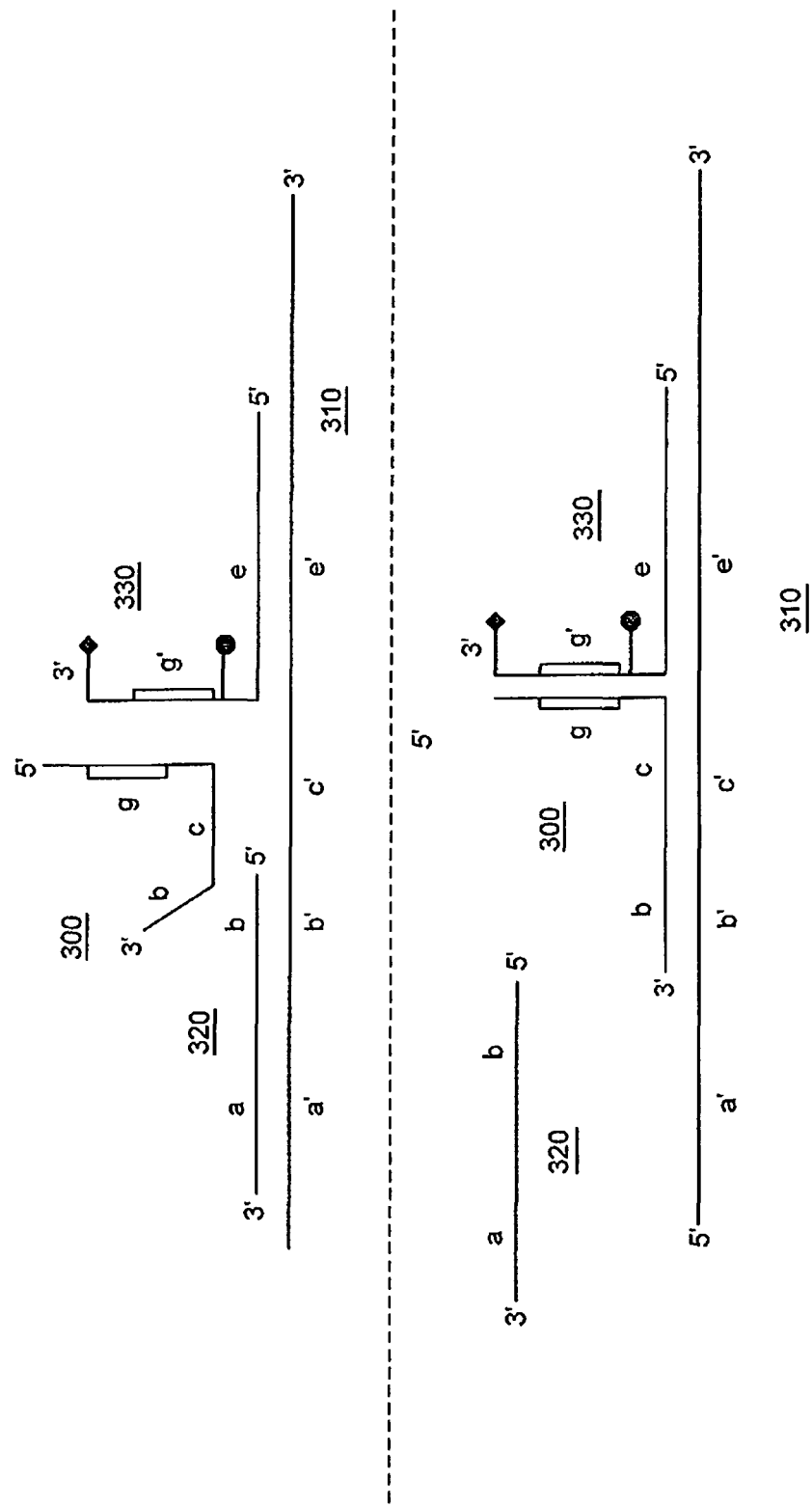
FIG. 6 illustrates an embodiment of the present invention that employs blocking probes.

FIG. 6 illustrates a further embodiment wherein blocking probes are used to enhance the specificity of probe hybridization. Blocker sequence 320 competes with Probe 300 for hybridization to a portion of the target sequence 310 to which probe 330 is hybridized. Displacement of the blocker sequence 320 by probe 300 depends upon the relative thermodynamic stability of the competing hybrid sequences (a, b):(a', b') and (b, c):(b', c'). To maximize specificity, probe 300 is designed such that only perfect complementarity between sequences (b, c) and (b', c') in the target 310 will lead to displacement of the blocking probe 320. The principles of such blocking technology are applicable to all embodiments described herein. One advantage provided by the use of the blocking probe 320 is in embodiments for the detection of single nucleotide polymorphisms where the difference in probe Tm between perfectly matched and a mismatched target sequences is small. Such blocking probes may be designed to be partially complementary to the target sequence, as illustrated in FIG. 6, or to one or more of the target-specific probes. In the case of the latter, hybridization of the probe to its specific target is thermodynamically favored over hybridization of the probe to the blocking oligonucleotide, thereby facilitating displacement of the blocking probe from the target in the presence of the target specific probe.

Generally, the nomenclature used herein is conventional in the molecular, biochemical, microbiological and recombinant DNA technologies. Such technologies are thoroughly explained in the literature. See, for example, "Molecular Cloning: A laboratory Manual" Sandbrook et al., (1989); "Current Protocols in Molecular Biology" Volumes I-III Ausubel, R. M., et ed. (1994); Cell Biology: A Laboratory Handbook" Volumes I-III Cellis, J. E., ed. (1994); "Current Protocols in Immunology" Volumes I-III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317 Academic Press.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference in the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of detecting the presence or absence of a target nucleic acid in a sample, comprising:
   a) preparing a sample suspected of containing a target nucleic acid;
   b) preparing a reaction mixture comprising the sample, first and second oligonucleotide probes, and a sequence specific endonuclease, wherein the first and second oligonucleotide probes each comprise a first sequence and a second sequence, wherein the first sequences of the first and second oligonucleotide probes are complementary with non-overlapping sequences of the target nucleic acid, and wherein the second sequences of each of the first and second oligonucleotide probes are complementary with each other, thus forming a duplex restriction site recognized by the sequence specific endonuclease, and wherein at least one of the first and second oligonucleotide probes comprises a detectable label positioned at one side of the restriction site, and a quenching moiety positioned at the other side of the restriction site, thus allowing the first sequences of the first and second oligonucleotide probes to selectively hybridize with the non-overlapping sequences of the nucleic acid of the target organism and the second sequences of the first and second oligonucleotide probes to selectively hybridize with each other and thereby form the duplex restriction site, such that, if the target nucleic acid is present in the sample, the sequence specific endonuclease cleaves the duplex at the restriction site, allowing for detection of the label, and denaturing the remaining portion of the oligonucleotide probes from the nucleic acid of the target organism and from each other.

2. The method of claim 1 wherein the sequence specific endonuclease is an enzyme selected from the group consisting of BsoBI, Hinc II, Ava I, Nci I and Fnu 4H.

3. The method of claim 2 wherein the sequence specific endonuclease is BsoBI.

4. The method of claim 1 wherein the reaction mixture is subjected to thermal cycling to denature the cleaved oligonucleotides from the target nucleic acid.

5. The method of claim 4 wherein the thermal cycling temperatures are selected with reference to a melting curve.

6. The method of claim 4 wherein the reaction mixture is maintained at a hybridization temperature that is greater than: i) the melting temperature of the first oligonucleotide probe to the target nucleic acid; ii) the melting temperature of the second oligonucleotide probe to the target nucleic acid; and iii) the melting temperature of a hybrid formed of the first oligonucleotide probe and the second oligonucleotide probe.

7. The method of claim 1 wherein the detectable label is a fluorophore.

8. The method of claim 7 wherein the fluorophore is a xanthene dye.

9. The method of claim 7 wherein the quencher is a rhodamine dye.

10. The method of claim 1 wherein the reaction mixture further comprises a blocking probe.

11. A method of detecting the presence or absence of a target nucleic acid in a sample, comprising:
a) preparing a sample suspected of containing target nucleic acid;
b) preparing a reaction mixture comprising the sample, first, second, and third oligonucleotide probes, and a sequence specific endonuclease wherein the first and second oligonucleotide probes each comprise a first sequence and a second sequence wherein the first sequences of the first and second oligonucleotide probes are complementary with non-overlapping sequences of the target nucleic acid, and wherein the second sequences of each of the first and second oligonucleotide probes are complementary with each other, thus forming a duplex restriction site and wherein the first and second oligonucleotide probes are non-labeled, and the second oligonucleotide probe further comprises a third sequence, at least a portion of which forms a hairpin with the second sequence of the second oligonucleotide probe that prevents the second oligonucleotide probe from hybridizing with the first oligonucleotide probe when the first and second oligonucleotide probes are not bound to the target nucleic acid, wherein the portion of the third sequence hybridizes with the third oligonucleotide probe to form a duplex restriction site; wherein the third oligonucleotide probe is a non-target specific oligonucleotide probe that comprises a detectable label positioned at one side of a first sequence that hybridizes with the third sequence of the second oligonucleotide probe to form the duplex restriction site, and a quenching moiety positioned at the other side of the first sequence of the third oligonucleotide probe;
if the target nucleic acid is present in the sample, allowing the first sequences of the first and second oligonucleotide probes to selectively hybridize with the non-overlapping sequences of the target nucleic acid;
thus allowing denaturation of the hairpin loop and hybridization between the second sequences of the first and second oligonucleotide probes, cleavage of the previously formed duplex at the restriction site by the sequence specific endonuclease, and separation of the third sequence from the second oligonucleotide probe, and dissociation of the first and second oligonucleotide probes from the target nucleic acid, and a plurality of cycles of: i) hybridization of the third sequence of the second oligonucleotide probe with the third oligonucleotide probe, thus forming a chemically modified duplex restriction site, ii) nicking a single strand of the chemically modified duplex restriction site by the sequence specific restriction endonuclease, iii) liberating label from quencher, and iv) dissociation of the third oligonucleotide probe from the third sequence of the second oligonucleotide probe; and
detecting signal generated from the label which indicates the presence of the target nucleic acid in the sample.

12. The method of claim 11 wherein the sequence specific endonuclease is an enzyme selected from the group consisting of BsoBI, Hinc II, Ava I, Nci I and Fnu 4H.

13. The method of claim 11 wherein the sequence specific endonuclease is BsoBI.

14. The method of claim 11 wherein the reaction mixture is subjected to thermal cycling to denature the cleaved oligonucleotides from the target nucleic acid.

15. The method of claim 14 wherein the thermal cycling temperatures are selected with reference to a melting curve.

16. The method of claim 14 wherein the reaction mixture is maintained at a hybridization temperature that is greater than:
i) the melting temperature of the first oligonucleotide probe to the target nucleic acid; ii) the melting temperature of the second oligonucleotide probe to the target nucleic acid; and iii) the melting temperature of a hybrid formed of the first oligonucleotide probe and the second oligonucleotide probe.

17. The method of claim 11 wherein the detectable label is a fluorophore.

18. The method of claim 17 wherein the fluorophore is a xanthene dye.

19. The method of claim 17 wherein the quencher is a rhodamine dye.

20. The method of claim 11 wherein the chemically modified restriction site is hemimodified.

21. The method of claim 11 wherein the reaction mixture further comprises a blocking probe.

22. A method of detecting the presence or absence of a target nucleic acid in a sample, comprising:
a) preparing a sample suspected of containing target nucleic acid;
b) preparing a reaction mixture comprising:
i) the sample:
ii) a first oligonucleotide probe having a first sequence and a second sequence, a second oligonucleotide probe having a first sequence and a second sequence, and a third oligonucleotide probe having a first sequence and a second sequence; and
iii) a sequence specific endonuclease, wherein
the first oligonucleotide probe has a first sequence that is complementary with a target nucleic acid sequence and a second sequence that is complementary with the first sequence of the second oligonucleotide probe wherein a first portion of the second sequence is a single stranded chemically modified portion of a restriction site, wherein a portion of the first and second sequences of the first oligonucleotide probe form a secondary structure;
the second oligonucleotide probe is a probe that does not hybridize directly to the target, wherein a portion of the first sequence of the second probe is complementary to the single stranded chemically modified portion of the second sequence of the first probe, and the second sequence of the second oligonucleotide probe is complementary with the first sequence of the third oligonucleotide probe wherein a portion of the second sequence of the second probe is a single stranded chemically modified portion of a restriction site, and the first sequence and the second sequence of the second oligonucleotide probe partially overlap and wherein at least portions of the first sequence and second sequence of the second oligonucleotide probe form a secondary structure;
the third oligonucleotide probe is a probe that does not hybridize directly to the target, wherein the first sequence includes a portion that is complementary to the single stranded chemically modified portion of a restriction site of the second oligonucleotide probe and further comprising a detectable label or quencher moiety positioned thereon and the second sequence forms a hairpin loop with a portion of the first sequence and has a detectable label or quencher moiety positioned thereon such that the quencher moiety blocks signal from the detectable label due to their relative positions on the third oligonucleotide probe;
and, if the target nucleic acid is present in the sample, allowing the target nucleic acid and the first sequence of the first oligonucleotide probe to selectively hybridize to form a first complex, in a plurality of cycles, i) allowing at least a portion of the second sequence of the first oligonucleotide probe and the first sequence of the second oligonucleotide probe to selectively hybridize to form a second complex; ii) cleaving a single strand portion of the duplex restriction site formed by the hybridization of the portion of the second sequence of the first oligonucleotide probe that forms the chemically modified single strand of the duplex restriction site with the complementary sequence on the second probe thereby separating the second sequence of the second oligonucleotide probe from the non-overlapping portion of the first sequence of the second oligonucleotide probe; and iii) dissociation of the second oligonucleotide probe from the first complex;

and, in a plurality of cycles, i) allowing the second sequence of the second oligonucleotide probe to selectively hybridize with the first sequence of the third oligonucleotide probe to form a third complex thereby separating label from quencher and liberating signal ii) cleaving a single strand duplex restriction site formed by hybridization of the portion of the second sequence of the second oligonucleotide probe with the complementary sequence on the first sequence of the third oligonucleotide probe, iii) liberating label from quencher; and iv) dissociation of the second sequence of the second oligonucleotide probe from the third oligonucleotide probe;

and detecting signal generated from the label which indicates the presence of the target nucleic acid in the sample.

23. The method of claim 22 wherein the secondary structure is a hairpin.

24. The method of claim 22 wherein the sequence specific endonuclease is an enzyme selected from the group consisting of BsoBI, Hinc II, Ava I, Nci I and Fnu 4H.

25. The method of claim 24 wherein the sequence specific endonuclease is BsoBI.

26. The method of claim 22 wherein the detectable label is a fluorophore.

27. The method of claim 26 wherein the quencher is a rhodamine dye.

28. The method of claim 22 wherein the fluorophore is a xanthene dye.

29. The method of claim 22 wherein the nucleic acid target sequence is a Human Papillomavirus nucleic acid.

30. The method of claim 29 wherein the Human Papillomavirus nucleic acid selected from the group consisting of Human Papillomavirus Type 16 and Human Papillomavirus Type 58.

31. The method of claim 30 wherein the target nucleic acid is selected from the Group consisting of SEQ ID NO. 2 and SEQ ID NO. 3.

32. The method of claim 22 wherein the first oligonucleotide probe is SEQ ID NO. 1, the second oligonucleotide probe is SEQ ID NO. 2 and the third oligonucleotide probe is SEQ ID NO. 3.

33. The method of claim 22 wherein the chemically modified restriction site is hemimodified.

34. The method of claim 22 wherein the reaction mixture further comprises a blocking probe.

* * * * *

SEQUENCE LISTING

```
<160> NUMBER OF SEQ ID NOS: 5

<210> SEQ ID NO 1
<211> LENGTH: 58
<212> TYPE: DNA
<213> ORGANISM: Artificial Sequence
<220> FEATURE:
<223> OTHER INFORMATION: Synthetic Probe

<400> SEQUENCE: 1
ccaaaattcc agtcctctct cgggtttttt agaggactgg aattttggtc tacaacct      58

<210> SEQ ID NO 2
```

```
<211> LENGTH: 50
<212> TYPE: DNA
<213> ORGANISM: Human papillomavirus type 16

<400> SEQUENCE: 2
gtgtgcctcc tgggggaggt tgtagaccaa aattccagtc ctccaaaata        50

<210> SEQ ID NO 3
<211> LENGTH: 50
<212> TYPE: DNA
<213> ORGANISM: Human papillomavirus type 58

<400> SEQUENCE: 3
aactggcaga cggaggaggt gttaaaccaa attgccagtc ctccaaaata        50

<210> SEQ ID NO 4
<211> LENGTH: 45
<212> TYPE: DNA
<213> ORGANISM: Artificial Sequence
<220> FEATURE:
<223> OTHER INFORMATION: Synthetic Probe

<400> SEQUENCE: 4
cactcctctc tcgagaaaaa aacccgagag aggagtggaa ttttg            45

<210> SEQ ID NO 5
<211> LENGTH: 40
<212> TYPE: DNA
<213> ORGANISM: Artificial Sequence
<220> FEATURE:
<223> OTHER INFORMATION: Synthetic Probe

<400> SEQUENCE: 5
gtttttttct cgagagagga ctgttttcag tcctctctcg                   40
```